US009579328B2

(12) United States Patent
Schiffman et al.

(10) Patent No.: US 9,579,328 B2
(45) Date of Patent: *Feb. 28, 2017

(54) PROSTAGLANDIN AND VASOCONSTRICTOR PHARMACEUTICAL COMPOSITIONS AND METHODS OF USE

(71) Applicant: ALLERGAN, INC., Irvine, CA (US)

(72) Inventors: Rhett M. Schiffman, Laguna Beach, CA (US); June Chen, San Juan Capistrano, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,289

(22) Filed: Jan. 7, 2016

(65) Prior Publication Data

US 2016/0354383 A1 Dec. 8, 2016

Related U.S. Application Data

(63) Continuation of application No. 13/868,854, filed on Apr. 23, 2013, now Pat. No. 9,248,135.

(60) Provisional application No. 61/637,597, filed on Apr. 24, 2012.

(51) Int. Cl.
| | |
|---|---|
| *A61K 31/5575* | (2006.01) |
| *A61K 31/138* | (2006.01) |
| *A61K 31/222* | (2006.01) |
| *A61K 31/5377* | (2006.01) |
| *A61K 45/06* | (2006.01) |
| *A61K 31/34* | (2006.01) |
| *A61K 31/4045* | (2006.01) |
| *A61K 31/4164* | (2006.01) |
| *A61K 31/4704* | (2006.01) |
| *A61K 31/498* | (2006.01) |
| *A61K 9/06* | (2006.01) |
| *A61K 9/08* | (2006.01) |
| *A61K 31/5355* | (2006.01) |
| *A61K 31/343* | (2006.01) |
| *A61K 31/404* | (2006.01) |
| *A61K 9/00* | (2006.01) |

(52) U.S. Cl.
CPC ........ *A61K 31/5575* (2013.01); *A61K 9/0048* (2013.01); *A61K 9/06* (2013.01); *A61K 9/08* (2013.01); *A61K 31/138* (2013.01); *A61K 31/222* (2013.01); *A61K 31/343* (2013.01); *A61K 31/404* (2013.01); *A61K 31/4164* (2013.01); *A61K 31/4704* (2013.01); *A61K 31/498* (2013.01); *A61K 31/5355* (2013.01)

(58) Field of Classification Search
None
See application file for complete search history.

(56) References Cited

U.S. PATENT DOCUMENTS

| 9,248,135 B2 | 2/2016 | Schiffman et al. |
| 2002/0010202 A1 | 1/2002 | Garst |
| 2014/0051704 A1 | 2/2014 | Chen et al. |
| 2014/0148455 A1 | 5/2014 | Likitlersuang et al. |

FOREIGN PATENT DOCUMENTS

| WO | 2011-087790 | 7/2011 |
| WO | 2011138801 | 11/2011 |
| WO | 2012-015998 | 2/2012 |
| WO | 2013-013143 | 1/2013 |

OTHER PUBLICATIONS

Abelson, Mark et al, Multicenter, Open-Label Evaluation of Hyperemia Associated With Use of Bimatoprost in Adults With Open-Angle Glaucoma or Ocular Hypertension, Advances in Therapy, Feb. 2003, 1-13, 20(1).
Aboulafia, Jeannine et al, Effect of Indomethacin and Prostaglandin on the Smooth Muscle Contracting Activity of Angiotensin and Other Agonists, Br. J. Pharmac., 1976, 223-228, 58.
Albrecht, Ester et al, Protective Role of Endothelial Nitric Oxide Synthase, Journal of Pathology, 2003, 8-17, 199.
Alster, Pawel et al, Effect of Nicotine on Prostacyclin Formation in Rat Aorta, European Journal of Pharmacology, 1983, 441-446, 86.
Astin, Maria et al, Mechanism of Prostaglandin E2-, F2α- and Latanoprost Acid-Induced Relaxation of Submental Veins, European Journal of Pharmacology, 1997, 195-201, 340.
Astin, Maria et al, Mediation of Prostaglandin f2α-Induced Ocular Surface Hyperemia by Sensory Nerves in Rabbits, Current Eye Research, 1997, 886-890, 16.
Astin, Maria et al, Role of Nitric oxide in PGF2α-Induced Ocular Hyperemia, Exp. Eye Res., 1994, 401-408, 59.
Astin, Maria, Effects of Prostaglandin E2, F2α, and Latanoprost Acid on Isolated Ocular Blood Vessels in Vitro, Journal of Ocular Pharmacology, 1998, 119-128, 14(2).
Botting, J.H. et al, The Effect of Indomethacin on the Release of Prostaglandin E2 and Acetylcholine From Guinea-Pig Isolated Ileum At Rrest and During Field Stimulation, Br. J. Pharmac., 1974, 119-124, 50.
Chen Zhou, Ph.D., Review and Evaluation of Phamacology/Toxicology Data, Center for Drug Evaluation and Research, Application No. 21-275, Jan. 18, 2001, pp. 1-107.
Chen, June et al, Conjunctival Hyperemia Related to Bimatoprost Treatment is Not Associated With Signs of Inflammation, Invest. Ophthalmol. Vis. Sci., 2004, 2609 (Abstract), 45.
Chen, June et al, Identification of a Prostanoid FP Receptor Population Producing Endothelium-Dependent Vasorelaxation in the Rabbit Jugular Vein, Bristish Journal of Dermtatology, 1995, 3035-3041, 116.
Chen, June et al, Studies Using Isolated Uterine and Other Preparations Show Bimatoprost and Prostanoid FP Agonists Have Different Activity Profiles, British Journal of Pharmacology, 2005, 493-501, 144.

(Continued)

*Primary Examiner* — Kristin Vajda
(74) *Attorney, Agent, or Firm* — Jonathan Bass

(57) ABSTRACT

Compositions containing a prostaglandin agent and a vasoconstrictor agent for ophthalmic applications are provided as well as methods of treating ophthalmic diseases using the same. In certain embodiments, the compositions and methods are useful for treating glaucoma without causing conjunctival hyperemia.

14 Claims, 6 Drawing Sheets

(56) References Cited

OTHER PUBLICATIONS

Christiansen, Gregory et al, Mechanism of Ocular Hypotensive Action of Bimatoprost (Lumigan) in Patients with Ocular Hypertension or Glaucoma, Ophthalmology, 2004, 1658-1662, 111.

Cirino, Giuseppe et al, Endothelial Nitric Oxide Synthase: The Cinderella of Inflammation?, Trends in Pharmacological Sciences, Feb. 2003, 91-95, 24(2).

Cohen, John et al, Two-Year Double-Masked Comparison of Bimatoprost with Timolol in Patients With Glaucoma or Ocular Hypertension, Survey of Ophthalmology, Mar. 2004, S45-S52, 49(1).

Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).

Eisenberg, Dan, Bimatoprost and Travoprost: A Review of Recent Studies of Two New Glaucoma Drugs, Survey of Ophthalmology, 2002, S105-S115, 47 (1).

Ferreira, S.H. et al, Prostaglandin Production by Rabbit Isolated Jejunum and Its Relationship to the Inherent Tone of the Preparation, Br. J. Pharmac., 1976, 469-477, 56.

Furchgott, Robert et al, The Obligatory Role of Endothelial cells in the Relaxation of Arterial Smooth Muscle by Acetylcholine, Nature, Nov. 1980, 373-376, 288.

Gandolfi, Stefano et al, Effect of Bimatoprost on Patients with Primary Open-Angle Glaucoma or Ocular Hypertension Who are Nonresponders to Latanprost, Ophthalmology, 2003, 609-614, 110.

Goodfriend, Theodore et al, Angiotensin Receptors in Bovine Umbilical Artery and Their Inhibition by Nonsteroidal Anti-Inflammatory Drugs, Br. J. Pharmac., 1981, 247-255, 72.

Guenoun, Jean-Marc et al, In Vitro Study of Inflammatory Potential and Toxicity Profile of Latanoprost, Travoprost, and Bimatoprost in Conjunctiva-Derived Epithelial Cells, Invest. Ophthalmol. Vis. Sci., 2005, 2444-2450, 46.

Haye-Legrand, Isabelle et al, Histamine Contraction of Isolated Human Airway Muscle Preparations: Role of Prostaglandins, The Journal of Pharmacology and Experimental Therapeutics, 1986, 536-541, 239(2).

Higginbotham, Eve et al, One-Year, Randomized Study Comparing Bimatoprost and Timolol in Glaucoma and Ocular Hypertension, Archives of Ophthalmology, Oct. 2002, 1286-1293, 120 (10), US.

International Search Report and Written Opinion mailed on Oct. 17, 2013 for PCT/US2013/037848 filed on Apr. 23, 2013 in the name of Allergan, Inc.

June Chen, Bimatoprost: Mechanism of Ocular Surface Hyperemia Associated with Topical Therapy, Cardiovascular Drug Reviews, 2005, 231-246, 23 (3).

Kass, Michael et al, The Ocular Hypertension Treatment Study: A Randomized Trial Determines That Topical Ocular Hypotensive Medication Delays or Prevents the Onset of Primary Open-Angle Glaucoma, Arch. Ophthalmol., 2002, 701-713, 120.

Kim, Jae Chan et al, The Role of Nitric Oxide in Ocular Surface Cells, J korean Med Sci, 2002, 389-394, 17.

Koss, Michael, Functional Role of Nitric Oxide in Regulation of Ocular Blood Flow, European Journal of Pharmacology, 1999, 161-174, 374.

Leal, Bruno et al, Conjunctival Hyperemia Associated With Bimatoprost Use: A Histopathologic Study, American Journal of Ophthalmology, Aug. 2004, 310-313, 138.

Martinez, Antonio et al., Efficacy and Safety of Bimatoprost/Timolol Fixed Combination in the Treatment of Glaucoma or Ocular Hypertension, Expert Opinion Pharmacotherapy, Jan. 1, 2008, 137-143, 9 (1).

Mroz, M. et al, Ocular Surface Changes Associated With the Use of Bimatoprost 0.03%, Invest. Ophthalmol. Vis. Sci., 2003, 4417 (Abstract), 44.

Noecker, Robert, Bimatoprost/Latanoprost Study Group. A Six Month Randomized Clinical Trial Comparing the Intraocular Pressure Lowering Efficacy of Bimatoprost and Latanoprost in Patients With Ocular Hypertension or Glaucoma, Am J Ophthal, 2003, 55-63, 135.

Northover, B.J., Mechanism of the Inhibitory Action of Indomethacin on Smooth Muscle, Br. J. Pharmac., 1971, 540-551, 41.

Parrish, Richard, A Comparison of Latanoprost, Bimatoprost, and Travoprost in Patients With Elevated Intraocular Pressure: A 12-Week, Randomized, Masked Evaluator Multicenter Study, Am J Ophthalmol, 2003, 688-703, 135.

Rees, D.D. et al, Characterization of Three Inhibitors of Endothelial Nitric Oxide Synthase In Vitro and In Vivo, Br. J. Pharmacol., 1990, 746-752, 101.

Sawdy, Robert et al, Effect of Nimesulide and Indomethacin on Contractility and the Ca2+ Channel Current in Myometrial Smooth Muscle From Pregnant Women, Br. J. Pharmac., 1998, 1212-1217, 125.

Schmetterer, Leopold et al, Role of Nitric Oxide in the Control of Ocular Blood Flow, Progess in Retinal and Eye Research, 2001, 823-847, 20(6).

Spada, C.S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).

Stewart, William et al, Conjunctival Hyperemia in Healthy Subjects After Short-Term Dosing With Latanoprost, Bimatoprost, and Travoprost, Am. J. Ophthalmol., Mar. 2003, 314-320, 135.

Williams, Robert, Efficacy of Bimatoprost in Glaucoma and Ocular Hypertension Unresponsive to Latanoprost, Advances in Therapy, Dec. 2002, 275-281, 19(6).

Woodward, David et al, Bimatoprost: a Novel Antiglaucoma Agent, Cardiovascular Drug Reviews, 2004, 103-120, 22(2).

Woodward, David et al, The Pharmacology of Bimatoprost (LumiganTM), Surv Ophthalmol, 2001, S337-S345, Suppl 4.

Woodward, David, Pharmacological Characterization of a Novel Antiglaucoma Agent, Bimatoprost (AGN 192024), J. Pharmacol. Exp. Ther., Jan. 24, 2003, 772-785, 305 (2).

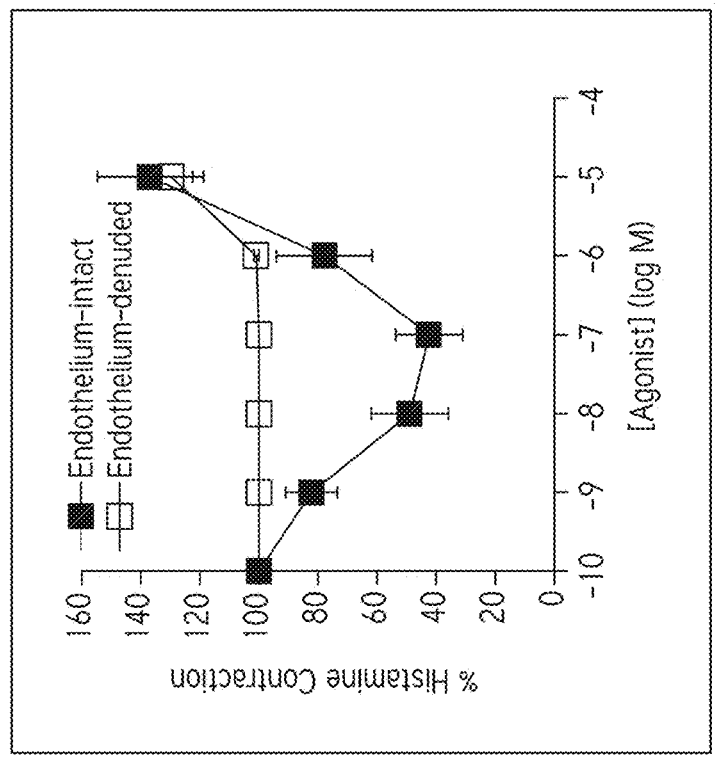
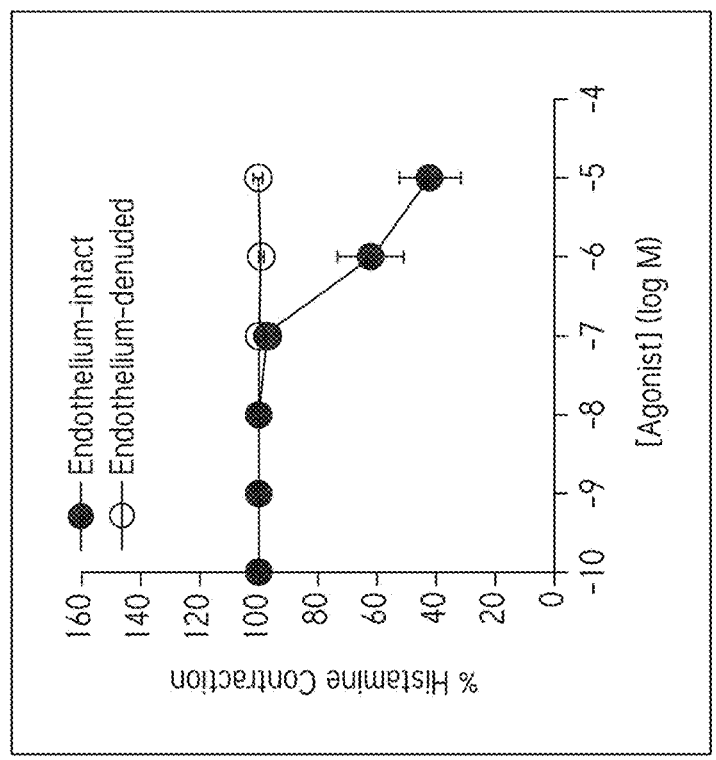
FIG. 3B
FIG. 3A

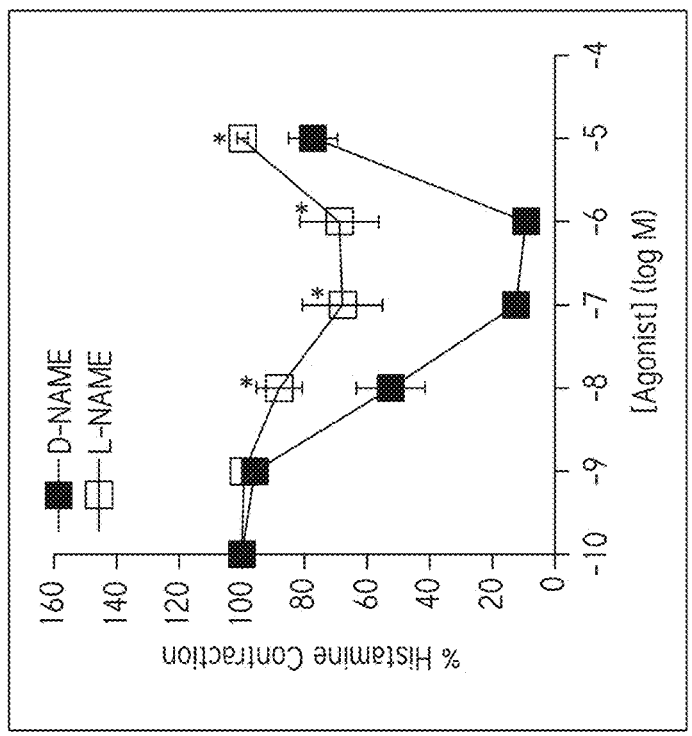
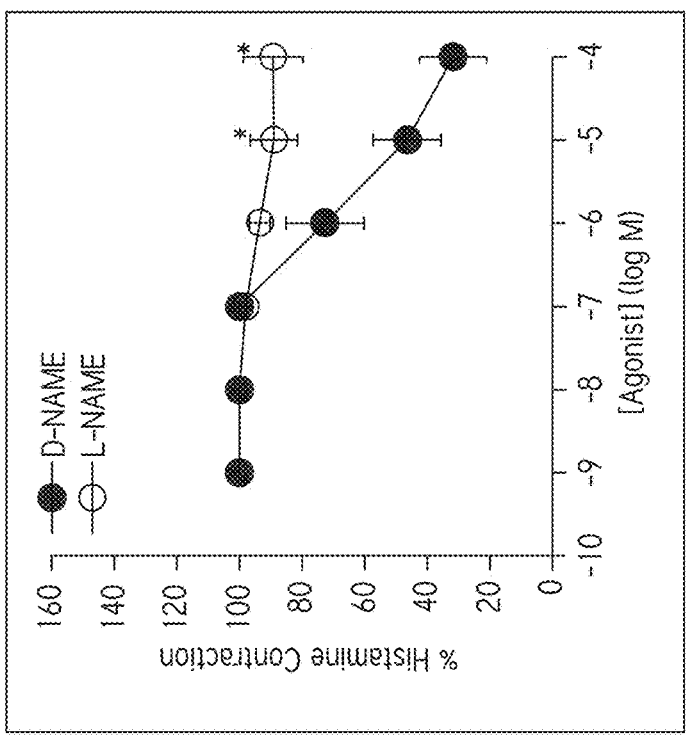
FIG. 5A
FIG. 5B

US 9,579,328 B2

PROSTAGLANDIN AND VASOCONSTRICTOR PHARMACEUTICAL COMPOSITIONS AND METHODS OF USE

CROSS REFERENCE TO RELATED APPLICATIONS

This application is a continuation of U.S. patent application Ser. No. 13/868,854, filed Apr. 23, 2013, which claims the benefit of U.S. Provisional Patent Application Ser. No. 61/637,597, filed Apr. 24, 2012, the disclosures of which are hereby incorporated in their entireties herein by reference.

BACKGROUND OF THE INVENTION

Based on its etiology, glaucoma can be classified into primary and secondary glaucoma. Primary glaucoma, also known as congenital glaucoma, can occur in the absence of other ocular conditions and its underlying causes are not known. However, it is known that increased intraocular pressure (IOP) observed in primary glaucoma is due to the obstruction of aqueous humor flow out of the eye. Secondary glaucoma results from another pre-existing ocular disease such as, uveitis, an intraocular tumor, enlarged cataract, central retinal vein occlusion, trauma to the eye, operative procedures and intraocular hemorrhage. Generally, any interference with the outward flow of aqueous humor from the posterior chamber into the anterior chamber and subsequently, into the canal of Schlemm can lead to secondary glaucoma.

Considering all types of glaucoma together, this ocular disorder occurs in about 2% of all persons over the age of 40. Unfortunately, glaucoma can be asymptomatic for years before progressing to a rapid loss of vision. In cases where surgery is not indicated, topical β-adrenoreceptor antagonists (or β-blockers) have traditionally been the drugs of choice for treating glaucoma. Further, certain prostaglandins and their analogues have been recommended for use in glaucoma management. For example, the prostaglandin analogue bimatoprost (Lumigan®) given at a dose of 0.03%, once daily, is a highly efficacious intraocular pressure (IOP) lowering drug. It has a very high systemic safety margin in studies conducted in laboratory animals. However, bimatoprost as well as many other topical anti-glaucoma medications produce conjunctival hyperemia as a side effect. Conjunctival hyperemia (or "red eye") refers to vasodilatation of the conjunctival blood vessels. The vasodilatation of the conjunctival blood vessels results in increased blood supply to the vessels or even rupture of the vessels, which causes redness of the eye, reduced visual acuity, severe ocular pain, and photophobia (light sensitivity).

The present invention solves these as well as other problems in the art by, inter alia, providing compositions of sub-therapeutic concentrations of a vasoconstrictor agent (e.g., a beta adrenergic antagonist) in combination with a pharmaceutically effective amount of a prostaglandin agent (e.g., is defined to include prostaglandins, prostaglandin analogs, prostaglandin derivatives or prostamides such as bimatoprost) and methods of using such compositions to treat ophthalmic diseases without causing conjunctival hyperemia.

BRIEF SUMMARY OF THE INVENTION

Presented herein are, inter alia, compositions containing a prostaglandin agent and a vasoconstrictor agent (e.g. at sub-therapeutic concentrations) for ophthalmic applications as well as methods of treating ophthalmic diseases. In certain embodiments, the compositions and methods are useful for treating the symptoms of glaucoma. The compositions and methods provided herein are particularly useful for treating increased intraocular pressure (IOP) without causing the adverse effect of conjunctival hyperemia.

In one aspect, a composition including a prostaglandin agent and a vasoconstrictor agent is provided. In another aspect, a method of reducing increased intraocular pressure (IOP) in a subject in need thereof is provided. The method includes administering to the subject a therapeutically effective amount of an ophthalmic pharmaceutical formulation including a prostaglandin agent and a vasoconstrictor agent.

Some embodiments of the invention include:
1. A composition comprising a prostaglandin agent and a vasoconstrictor agent.
2. The composition of paragraph 1, wherein said composition is an ophthalmic pharmaceutical formulation further comprising an ophthalmically acceptable excipient.
3. The composition of paragraph 1, wherein said prostaglandin agent is present in a therapeutically effective amount.
4. The composition of paragraph 1, wherein said vasoconstrictor agent is present in a sub-therapeutic amount.
5. The composition of paragraph 2, wherein said prostaglandin agent and said vasoconstrictor agent are present in a combined amount effective to treat an ophthalmic disease.
6. The composition of paragraph 2, wherein said ophthalmic pharmaceutical formulation is a gel formulation.
7. The composition of paragraph 2, wherein said ophthalmic pharmaceutical formulation is an aqueous solution.
8. The composition of paragraph 2, wherein said prostaglandin agent is bimatoprost.
9. The composition of paragraph 8, wherein said bimatoprost is present in an amount approximately equal to or less than about 0.1% w/w.
10. The composition of paragraph 8, wherein said bimatoprost is present in an amount of about 0.03% w/w.
11. The composition of paragraph 2, wherein said prostaglandin agent is travoprost.
12. The composition of paragraph 11, wherein said travoprost is present in an amount approximately equal to or less than about 0.1% w/w.
13. The composition of paragraph 11, wherein said travoprost is present in an amount of about 0.004% w/w.
14. The composition of paragraph 2, wherein said prostaglandin agent is latanoprost.
15. The composition of paragraph 14, wherein said latanoprost is present in an amount approximately equal to or less than about 0.1% w/w.
16. The composition of paragraph 14, wherein said latanoprost is present in an amount of about 0.005% w/w.
17. The composition of paragraph 2, wherein said vasoconstrictor agent is an alpha adrenergic agonist.
18. The composition of paragraph 2, wherein said vasoconstrictor agent is a beta adrenergic antagonist.
19. The composition of paragraph 18, wherein said beta adrenergic antagonist is timolol.
20. The composition of paragraph 19, wherein said timolol is present in a sub-therapeutic amount.
21. The composition of paragraphs 18 or 20, wherein said sub-therapeutic amount is an amount less than about 0.25% w/w or less than 0.1% w/w or less than 0.05% w/w or in a range from 0.0001%-0.001% w/w.
22. The composition of paragraph 19, wherein said timolol is timolol maleate.
23. The composition of paragraph 19, wherein said timolol is timolol hemihydrate.

24. The composition of paragraph 18, wherein said beta adrenergic antagonist is betaxolol.
25. The composition of paragraph 24, wherein said betaxolol is present in a sub-therapeutic amount.
26. The composition of paragraph 25, wherein said sub-therapeutic amount is an amount less than about 0.05% w/w or in an amount less than 0.005% w/w.
27. The composition of paragraph 24, wherein said betaxolol is a betaxolol salt.
28. The composition of paragraph 18, wherein said beta adrenergic antagonist is levobunolol.
29. The composition of paragraph 28, wherein said levobunolol is present in a sub-therapeutic amount.
30. The composition of paragraph 29, wherein said sub-therapeutic amount is an amount less than about 0.25% w/w or less than 0.025% w/w.
31. The composition of paragraph 28, wherein said levobunolol is a levobunolol salt.
32. The composition of paragraph 18, wherein said beta adrenergic antagonist is metipranolol.
33. The composition of paragraph 32, wherein said metipranolol is present in a sub-therapeutic amount.
34. The composition of paragraph 33, wherein said sub-therapeutic amount is an amount less than about 0.3% w/w or 0.03% w/w.
35. The composition of paragraph 32, wherein said metipranolol is a metipranolol salt.
36. The composition of paragraph 2, further comprising a buffering agent, a tonicity agent, a salt, and a preservative.
37. The composition of paragraph 2, consisting essentially of bimatoprost, timolol, a buffering agent, a tonicity agent, a salt, a thickening agent and a preservative.
38. The composition of paragraph 37, wherein said timolol is present in a sub-therapeutic amount.
39. The composition of paragraph 38, wherein said sub-therapeutic amount is an amount less than about 0.25% w/w or less than 0.05% w/w or 0.005% w/w.
40. The composition of paragraph 2, consisting essentially of bimatoprost, betaxolol, a buffering agent, a tonicity agent, a salt, a thickening agent and a preservative.
41. The composition of paragraph 40, wherein said betaxolol is present in a sub-therapeutic amount.
42. The composition of paragraph 41, wherein said sub-therapeutic amount is an amount less than about 0.25% w/w.
43. The composition of paragraph 2, consisting essentially of bimatoprost, levobunolol, a buffering agent, a tonicity agent, a salt, a thickening agent and a preservative.
44. The composition of paragraph 43, wherein said levobunolol is present in a sub-therapeutic amount.
45. The composition of paragraph 44, wherein said sub-therapeutic amount is an amount less than about 0.25% w/w.
46. The composition of paragraph 2, consisting essentially of bimatoprost, metipranolol, a buffering agent, a tonicity agent, a salt, a thickening agent and a preservative.
47. The composition of paragraph 46, wherein said metipranolol is present in a sub-therapeutic amount.
48. The composition of paragraph 47, wherein said sub-therapeutic amount is an amount less than about 0.3% w/w.
49. A method of reducing intraocular pressure (IOP) in a subject in need thereof, said method comprising:
administering to said subject a therapeutically effective amount of an ophthalmic pharmaceutical formulation comprising a prostaglandin agent and a vasoconstrictor agent.
50. The method of paragraph 49, wherein said prostaglandin agent is present in a therapeutically effective amount and said vasoconstrictor agent is present in a sub-therapeutic amount.
51. The method of paragraph 49, wherein said prostaglandin agent is bimatoprost and wherein said vasoconstrictor agent is timolol.
52. The method of paragraph, wherein timolol is present in an amount less than about 0.25% w/w.
53. The method of paragraph 49, wherein said ophthalmic pharmaceutical formulation further comprises a buffering agent, a tonicity agent, a salt, a thickening agent and a preservative.
54. The method of paragraph 49, wherein said ophthalmic pharmaceutical formulation consists essentially of bimatoprost, timolol, a buffering agent, a tonicity agent, a salt, a thickening agent and a preservative.
55. The method of paragraph 54, wherein bimatoprost is present in a therapeutically effective amount and the timolol is present in a sub-therapeutic amount.
56. The composition of paragraph 4, wherein the vasoconstrictor is selected from the group consisting of befunolol, betaxolol, carteolol, levobunolol, metipranolol, timolol, brimonidine, tetrahydrozolone hydrochloride and mepindolol.
57. The composition of paragraph 56, where the vasoconstrictor is present in an amount selected from the group consisting of 0.01 to about 0.06, from about 0.02 to about 0.06, from about 0.03 to about 0.06, from about 0.04 to about 0.06, from about 0.05 to about 0.06, from about 0.001 to about 0.04, from about 0.002 to about 0.04, from about 0.003 to about 0.04, from about 0.004 to about 0.04, from about 0.005 to about 0.04, from about 0.006 to about 0.04, from about 0.007 to about 0.04, from about 0.008 to about 0.04, from about 0.009 to about 0.04, from about 0.01 to about 0.04, from about 0.02 to about 0.04, from about 0.03 to about 0.04, from about 0.001 to about 0.02, from about 0.002 to about 0.02, from about 0.003 to about 0.02, from about 0.004 to about 0.02, from about 0.005 to about 0.02, from about 0.006 to about 0.02, from about 0.007 to about 0.02, from about 0.008 to about 0.02, from about 0.009 to about 0.02, from about 0.01 to about 0.02, from about 0.001 to about 0.01, from about 0.002 to about 0.01, from about 0.003 to about 0.01, from about 0.004 to about 0.01, from about 0.005 to about 0.01, from about 0.006 to about 0.01, from about 0.007 to about 0.01, from about 0.008 to about 0.01, or from about 0.009 to about 0.01% (w/w).

BRIEF DESCRIPTION OF THE DRAWINGS

FIG. 3. Concentration-response curves for (FIG. 3A) bimatoprost and (FIG. 3B) latanoprost free acid in histamine-precontracted endothelium-intact and endothelium-denuded rabbit isolated jugular veins. Results are expressed as mean±S.E.M. of 5-6 animals. FIG. 3A adapted from Chen J et al., *Invest Ophthalmol Vis Sci* 2004; 45:ARVO E-Abstract 2609; FIG. 3B extends results reported in Chen J et al., *Invest Ophthalmol Vis Sci* 2004; 45:ARVO E-Abstract 2609; and Pharmacology Review of New Drug Application 21-275. FDA/Center for Drug Evaluation and Research. 2001;Part 1 and Part 2:1-107. Available online at http://www.fda.gov/cder/foi/nda/2001/21275_Lumigan.htm.

FIG. 5. Concentration-response curves for (FIG. 5A) bimatoprost and (FIG. 5B) latanoprost free acid in the presence of 100 µM L-NAME or 100 (µM D-NAME control in endothelium-intact rabbit isolated jugular veins. Results are expressed as mean±S.E.M. of 6 animals. *$P \leq 0.05$, compared to responses in D-NAME pretreated tissues at the same concentration, paired t-test.

DETAILED DESCRIPTION OF THE INVENTION

Figure 1:
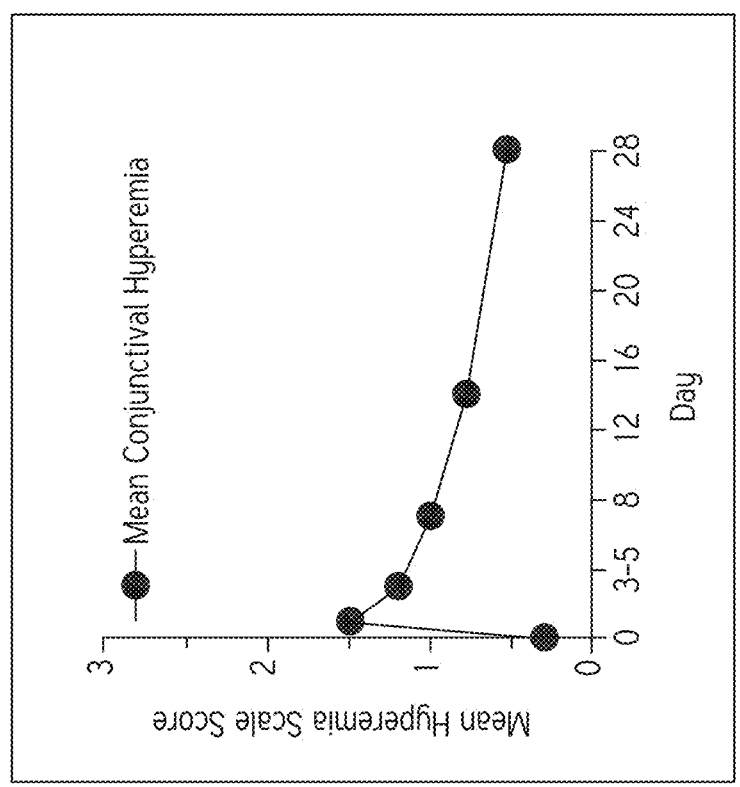
FIG. 1. Conjunctival hyperemia scale scores at each study visit in patients treated with topically applied bimatoprost 0.03% once daily. Results are expressed as the mean hyperemia score of three vessel-bed scores from 33-39 patients with bilateral open-angle glaucoma or ocular hypertension. Adapted from Abelson M B et al., *Adv. Ther.* 2003; 20:1-13.

The terms "a," "an," or "the" as used herein not only include aspects with one member, but also aspects with more than one member. For example, an embodiment including "a buffer and a chelating agent" should be understood to present aspects with at least a second buffer, at least a second chelating agent, or both.

The term "or" as used herein should in general be construed non-exclusively. For example, an embodiment of "a formulation including A or B" would typically present an aspect with a formulation including both A and B. "Or" should, however, be construed to exclude those aspects presented that cannot be combined without contradiction (e.g., a formulation pH that is between 9 and 10 or between 7 and 8).

"Agent" as used herein indicates a compound or mixture of compounds that, when added to a pharmaceutical formulation, tend to produce a particular effect on the formulation's properties. For example, a formulation including a thickening agent is likely to be more viscous than an otherwise identical comparative formulation that lacks the thickening agent.

"Formulation," "composition," and "preparation" as used herein are equivalent terms referring to a composition of matter suitable for pharmaceutical use (i.e., producing a therapeutic effect as well as possessing acceptable pharmacokinetic and toxicological properties).

As used herein, the term "pharmaceutically" acceptable is used as equivalent to physiologically acceptable. In certain embodiments, a pharmaceutically acceptable composition or preparation will include agents for buffering and preservation in storage, and can include buffers and carriers for appropriate delivery, depending on the route of administration.

As used herein, the terms "prevent" and "treat" are not intended to be absolute terms. Treatment can refer to any delay in onset, e.g., reduction in the frequency or severity of symptoms, amelioration of symptoms, improvement in patient comfort, and the like. The effect of treatment can be compared to an individual or pool of individuals not receiving a given treatment, or to the same patient before, or after cessation of, treatment.

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes all members of the animal kingdom prone to suffering from the indicated disorder. In some aspects, the subject is a mammal, and in some aspects, the subject is a human.

The terms "effective amount," "therapeutically effective amount" or "pharmaceutically effective amount" as used herein refer to that amount of the therapeutic agent sufficient to ameliorate one or more aspects of the disorder. The result can be reduction and/or alleviation of the signs, symptoms, or causes of a disease, or any other desired alteration of a biological system. For example, an "effective amount" for therapeutic uses is the amount of the composition comprising an agent as set forth herein required to provide a clinically significant decrease in an ophthalmic disease. For example, for the given aspect (e.g., length of incidence), a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. An appropriate "effective" amount in any individual case may be determined using techniques, such as a dose escalation study.

The term "sub-therapeutic amount" or "sub-therapeutic concentration" as provided herein refers to an amount of a therapeutic agent (e.g. drug) that is insufficient to provide a therapeutic effect in the absence of an additional active agent. In some embodiments, the sub-therapeutic amount is less than the clinically approved amount or concentration of that therapeutic agent. In some embodiments, a sub-therapeutic amount is less than the lowest clinically approved amount of a therapeutic agent. A clinically approved amount of a therapeutic agent is the amount approved by the U.S. Food and Drug Administration (FDA) or an equivalent regulatory entity, to be safe and effective when used as directed.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "disease" refers to any deviation from the normal health of a mammal and includes a state when disease symptoms are present, as well as conditions in which a deviation (e.g., infection, gene mutation, genetic defect, etc.) has occurred, but symptoms are not yet manifested. According to the present invention, the methods disclosed herein are suitable for use in a patient that is a member of the Vertebrate class, Mammalia, including, without limitation, primates, livestock and domestic pets (e.g., a companion animal). Typically, a patient will be a human patient.

As used herein, "topical application," "topical administration," and "topically administering" are used interchangeably herein and include the administration of a composition to the eye, the mucosal or dermal area proximal to the eye. Topical application or administering may result in the delivery of an active agent to the eye or skin, a localized region of the body, a localized volume of the body, or the systemic circulation.

"Topical formulation" and "topical pharmaceutical composition" are used interchangeably herein and include a formulation that is suitable for topical application to the eye or dermal area proximal to the eye, or other localized region of the body. A topical formulation may, for example, be used to confer a therapeutic benefit to its user. Specific topical formulations can be used for topical, local, regional, or transdermal application of substances.

As used herein, the terms "application," "apply," and "applying" used in reference to a topical composition product or method of using a composition or a product, refer to any manner of administering a topical composition or a product to the eye, the mucosal or dermal area proximal to the eye of a patient which, in medical or cosmetology practice, delivers the composition or the product to patient's eye, the mucosal or dermal area proximal to the eye. Smearing, rubbing, spreading, spraying a topical composition, with or without the aid of suitable devices, on a patient's skin are all included within the scope of the term "application," as used herein. The term "topical" or "topically" in reference to administration or application of a composition or a product refers to epicutaneous administration or application, or administration onto skin. The term "topically active agent" as used herein refers to a compound that is effective in a treatment of a skin condition when administered topically. It is to be understood that a topically active agent can have a local or a systemic effect, or both, when administered topically. The term "topical," when used in reference to a composition or a product refers to a composition or a product formulated for topical application.

The terms "adverse effect" or "side effects" as used herein refer to a harmful and undesired effect associated with the use of a medication (i.e. drug). An adverse effect may be termed a side effect, when judged to be secondary to a main or therapeutic effect. Adverse effects or side effects may occur when starting treatment, increasing treatment dosage or discontinuing treatment with a drug. Adverse effects may also be caused by drug interaction when more than one drug is administered. In some embodiments, the side effect of administering therapeutically effective amounts The abbreviations used herein have their conventional meaning within the chemical, biological or pharmaceutical arts.

The terms "about" and "approximately equal" are used herein to modify a numerical value and indicate a defined range around that value. If "X" were the value, "about X" or "approximately equal to X" would generally indicate a value from 0.90X to 1.10X. Any reference to "about X" minimally indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids. Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

In formulations including an "additional," "further," or "second" component, the second component as used herein is chemically different from the other components or first component.

A "third" component is different from the other, first, and second components, and further enumerated or "additional" components are similarly different.

The term "hydrophobic" is used herein in accordance with its plain ordinary meaning and refers to a chemical group having a tendency to attract non-polar or uncharged chemical groups, e.g. hexane, and to repel polar or charged chemical groups, e.g. water.

"Conjunctival hyperemia" or "red eye" refers to an ophthalmic condition caused by vasodilatation of the conjunctival blood vessels. The vasodilatation of the conjunctival blood vessels results in increased blood supply to the vessels or even rupture of the vessels, which causes redness of the eye, reduced visual acuity, severe ocular pain, and photophobia (light sensitivity). Conjunctival hyperemia is a common side effect caused by many topical glaucoma medications (e.g., bimatoprost or Lumigan®).

I. Compositions

The present invention provides pharmaceutical compositions including a pharmaceutically active ingredient (e.g., two pharmaceutically active ingredients) and an ophthalmically acceptable excipient. In some embodiments, the pharmaceutical composition includes a prostaglandin agent and a vasoconstrictor agent. In some embodiments, the vasoconstrictor agent is present in a sub-therapeutic amount. The compositions provided herein may be used for the treatment of ophthalmic diseases. In some embodiments, the compositions are used for the treatment of increased intraocular pressure (IOP). Gels, aqueous solutions, emulsions, creams or ointments are contemplated as useful pharmaceutical formulations including the compositions provided herein.

In one aspect, a composition including a prostaglandin agent and a vasoconstrictor agent is provided. In some embodiments, the composition is an ophthalmic pharmaceutical formulation further including an ophthalmically acceptable excipient. Generally, ophthalmically acceptable excipients commonly known in the fields of ophthalmology and cosmetology as useful in topical compositions, and any non-toxic, inert, and effective topical carriers, are contemplated as useful in the compositions and products according to the embodiments of the present invention.

In some embodiments, the prostaglandin agent is present in a therapeutically effective amount. In other embodiments, the vasoconstrictor agent is present in a sub-therapeutic amount. As described above a sub-therapeutic amount is an amount of a therapeutic agent (e.g. drug), which is different to the clinically approved amount or concentration of that therapeutic agent. Thus, when a therapeutic agent (e.g. drug) is present at a sub-therapeutic amount it may be present at an amount that is less than the clinically approved amount for that therapeutic agent. In some embodiments, a sub-therapeutic amount of a therapeutic agent is less than the lowest clinically approved amount of that therapeutic agent.

Where the ophthalmic compositions provided herein include more than one active pharmaceutical ingredient, the active pharmaceutical ingredients are present in a combined amount effective to treat ophthalmic diseases. A combined effective amount is the total amount of active pharmaceutical ingredients that, in combination, provide an effective amount. For example, a combined effective amount may include a first amount of a first active pharmaceutical ingredient (e.g. a prostaglandin agent) and a second amount of a second active pharmaceutical ingredient (e.g. a vasoconstrictor agent). The first amount of the first active pharmaceutical ingredient may be less than an effective amount of the first active pharmaceutical ingredient when the first active pharmaceutical ingredient is administered without the second active pharmaceutical ingredient. On the other hand, the first amount of the first active pharmaceutical ingredient may be more than an effective amount of the first active pharmaceutical ingredient when the first active pharmaceutical ingredient is administered without the second active pharmaceutical ingredient. Correspondingly, the second amount of the second active pharmaceutical ingredient may be less than an effective amount of the second active pharmaceutical ingredient when the second active pharmaceutical ingredient is administered without the first active pharmaceutical ingredient. Equally, the second amount of the second active pharmaceutical ingredient may be more than an effective amount of the second active pharmaceutical ingredient when the second active pharmaceutical ingredient is administered without the first active pharmaceutical ingredient. Thus, in some embodiments, the prostaglandin agent and the vasoconstrictor agent are present in a combined amount effective to treat ophthalmic diseases.

The ophthalmic pharmaceutical compositions provided herein may be administered in various ways e.g., a foam, a gel, a cream, jelly, solution, suspension, a spray (e.g., a solution), an ointment, ointment films, occlusive films, sustained release films, fast drying films, slow drying films, patches, semi solids or stick formulation comprising a semi-solid vehicle with a melting point near physiological temperature. Topical compositions and products according to embodiments of the present invention can be formulated as creams, which can be semi-solid emulsions of oil and water, and lotions, including suspensions of powdered material in water or alcohol base and water-based emulsions. Topical compositions and products according to embodiments of the present invention can also be formulated as ointments, which are oleaginous and contain little if any water. In some embodiments, the ophthalmic pharmaceutical formulation is a gel formulation. In other embodiments, the ophthalmic pharmaceutical formulation is an aqueous formulation.

The compositions provided herein may include a prostaglandin agent and a vasoconstrictor agent as active pharmaceutical ingredients. It is also to be understood that pharmaceutically acceptable salts of the active pharmaceutical ingredients may be included in the compositions provided herein. A prostaglandin agent is a compound capable of binding a prostaglandin $E_2$ receptor. A prostaglandin $E_2$ receptor as defined herein is a G-protein coupled receptor that is being bound by prostaglandin $E_2$. Prostaglandin $E_2$ is a lipid mediator that is derived enzymatically from fatty acids and has important functions in the animal body. $E_2$ prostaglandins have a variety of strong physiological effects, such as regulating the contraction and relaxation of smooth muscle tissue. Non-limiting examples of prostaglandin agents contemplated for the compositions and methods provided herein are travoprost, latanoprost, unoprostone, tafluprost and bimatoprost. In some embodiments, the prostaglandin agent is bimatoprost. Bimatoprost refers, in the customary sense, to CAS Registry No. 155206-00-1. In some embodiments, bimatoprost is present in an amount approximately equal to or less than about 0.1% w/w. In some embodiments, bimatoprost is present from about 0.001 to about 0.1, from about 0.002 to about 0.1, from about 0.003 to about 0.1, from about 0.004 to about 0.1, from about 0.005 to about 0.1, from about 0.006 to about 0.1, from about 0.007 to about 0.1, from about 0.008 to about 0.1, from about 0.009 to about 0.1, from about 0.01 to about 0.1, from about 0.02 to about 0.1, from about 0.03 to about 0.1, from about 0.04 to about 0.1, from about 0.05 to about 0.1, from about 0.06 to about 0.1, from about 0.07 to about 0.1, from about 0.08 to about 0.1, from about 0.09 to about 0.1, from about 0.001 to about 0.08, from about 0.002 to about 0.08, from about 0.003 to about 0.08, from about 0.004 to about 0.08, from about 0.005 to about 0.08, from about 0.006 to about 0.08, from about 0.007 to about 0.08, from about 0.008 to about 0.08, from about 0.009 to about 0.08, from about 0.01 to about 0.08, from about 0.02 to about 0.08, from about 0.03 to about 0.08, from about 0.04 to about 0.08, from about 0.05 to about 0.08, from about 0.06 to about 0.08, from about 0.07 to about 0.08, from about 0.001 to about 0.06, from about 0.002 to about 0.06, from about 0.003 to about 0.06, from about 0.004 to about 0.06, from about 0.005 to about 0.06, from about 0.006 to about 0.06, from about 0.007 to about 0.06, from about 0.008 to about 0.06, from about 0.009 to about 0.06, from about 0.01 to about 0.06, from about 0.02 to about 0.06, from about 0.03 to about 0.06, from about 0.04 to about 0.06, from about 0.05 to about 0.06, from about 0.001 to about 0.04, from about 0.002 to about 0.04, from about 0.003 to about 0.04, from about 0.004 to about 0.04, from about 0.005 to about 0.04, from about 0.006 to about 0.04, from about 0.007 to about 0.04, from about 0.008 to about 0.04, from about 0.009 to about 0.04, from about 0.01 to about 0.04, from about 0.02 to about 0.04, from about 0.03 to about 0.04, from about 0.001 to about 0.02, from about 0.002 to about 0.02, from about 0.003 to about 0.02, from about 0.004 to about 0.02, from about 0.005 to about 0.02, from about 0.006 to about 0.02, from about 0.007 to about 0.02, from about 0.008 to about 0.02, from about 0.009 to about 0.02, from about 0.01 to about 0.02, from about 0.001 to about 0.01, from about 0.002 to about 0.01, from about 0.003 to about 0.01, from about 0.004 to about 0.01, from about 0.005 to about 0.01, from about 0.006 to about 0.01, from about 0.007 to about 0.01, from about 0.008 to about 0.01, or from about 0.009 to about 0.01% (w/w). In some embodiments, bimatoprost is present at about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, or 0.1% (w/w). In some embodiments, bimatoprost is present in an amount of about 0.03% w/w.

In other embodiments, the prostaglandin agent is travoprost. Travoprost refers, in the customary sense, to CAS Registry No. 157283-68-6. In some embodiments, the travoprost is present in an amount approximately equal to or less than about 0.1% w/w. In some embodiments, the travoprost is present in an amount from about 0.0002 to about 0.1, from about 0.0004 to about 0.1, from about 0.0006 to about 0.1, from about 0.0008 to about 0.1, from about 0.001 to about 0.1, from about 0.002 to about 0.1, from about 0.004 to about 0.1, from about 0.006 to about 0.1, from about 0.008 to about 0.1, from about 0.01 to about 0.1, from about 0.02 to about 0.1, from about 0.04 to about 0.1, from about 0.06 to about 0.1, from about 0.08 to about 0.1, from about 0.0002 to about 0.08, from about 0.0004 to about 0.08, from about 0.0006 to about 0.08, from about 0.0008 to about 0.08, from about 0.001 to about 0.08, from about 0.002 to about 0.08, from about 0.004 to about 0.08, from about 0.006 to about 0.08, from about 0.008 to about 0.08, from about 0.01 to about 0.08, from about 0.02 to about 0.08, from about 0.04 to about 0.08, from about 0.06 to about 0.08, from about 0.0002 to about 0.06, from about 0.0004 to about 0.06, from about 0.0006 to about 0.06, from about 0.0008 to about 0.06, from about 0.001 to about 0.06, from about 0.002 to about 0.06, from about 0.004 to about 0.06, from about 0.006 to about 0.06, from about 0.008 to about 0.06, from about 0.01 to about 0.06, from about 0.02 to about 0.06, from about 0.04 to about 0.06, from about 0.0002 to about 0.04, from about 0.0004 to about 0.04, from about 0.0006 to about 0.04, from about 0.0008 to about 0.04, from about 0.001 to about 0.04, from about 0.002 to about 0.04, from about 0.004 to about 0.04, from about 0.006 to about 0.04, from about 0.008 to about 0.04, from about 0.01 to about 0.04, from about 0.02 to about 0.04, from about 0.0002 to about 0.02, from about 0.0004 to about 0.02, from about 0.0006 to about 0.02, from about 0.0008 to about 0.02, from about 0.001 to about 0.02, from about 0.002 to about 0.02, from about 0.004 to about 0.02, from about 0.006 to about 0.02, from about 0.008 to about 0.02, from about 0.01 to about 0.02, from about 0.0002 to about 0.01, from about 0.0004 to about 0.01, from about 0.0006 to about 0.01, from about 0.0008 to about 0.01, from about 0.001 to about 0.01, from about 0.002 to about 0.01, from about 0.004 to about 0.01, from about 0.006 to about 0.01, from about 0.008 to about 0.01, from about 0.0002 to about 0.008, from about 0.0004 to about 0.008, from about 0.0006 to about 0.008, from about 0.0008 to about 0.008, from about 0.001 to about 0.008, from about 0.002 to about 0.008, from about 0.004 to about 0.008, from about 0.006 to about 0.008, from about 0.0002 to about 0.006, from about 0.0004 to about 0.006, from about 0.0006 to about 0.006, from about 0.0008 to about 0.006, from about 0.001 to about 0.006, from about 0.002 to about 0.006, from about 0.004 to about 0.006, from about 0.0002 to about 0.004, from about 0.0004 to about 0.004, from about 0.0006 to about 0.004, from about 0.0008 to about 0.004, from about 0.001 to about 0.004, from about 0.002 to about 0.004, from about 0.0002 to about 0.002, from about 0.0004 to about 0.002, from about 0.0006 to about 0.002, from about 0.0008 to about 0.002, from about 0.001 to about 0.002, from about 0.0002 to about 0.001, from about 0.0004 to about 0.001, from about 0.0006 to about 0.001, from about 0.0008 to about 0.001, from about 0.0002 to about 0.0008, from about 0.0004 to about 0.0008, from about 0.0006 to about 0.0008, from about 0.0002 to about 0.0006, from about 0.0004 to about 0.0006, or from about 0.0002 to about 0.0004% (w/w). In some embodiments, the travoprost is present at about 0.1, 0.08, 0.06, 0.04, 0.02, 0.01, 0.008, 0.006, 0.004, 0.002, 0.001, 0.0008, 0.0006, 0.0004, or 0.0002% (w/w). In some embodiments, travoprost is present in an amount of about 0.004% w/w.

In some embodiments, the prostaglandin agent is latanoprost. Latanoprost refers, in the customary sense, to CAS Registry No. 130209-82-4. In some embodiments, the latanoprost is present in an amount approximately equal to or less than about 0.1% w/w. In some embodiments, latanoprost is present from about 0.0003 to about 0.1, from about 0.0005 to about 0.1, from about 0.0007 to about 0.1, from about 0.0009 to about 0.1, from about 0.001 to about 0.1, from about 0.003 to about 0.1, from about 0.005 to about 0.1, from about 0.007 to about 0.1, from about 0.009 to about 0.1, from about 0.01 to about 0.1, from about 0.03 to about 0.1, from about 0.05 to about 0.1, from about 0.07 to about 0.1, from about 0.09 to about 0.1, from about 0.0003 to about 0.09, from about 0.0005 to about 0.09, from about 0.0007 to about 0.09, from about 0.0009 to about 0.09, from about 0.001 to about 0.09, from about 0.003 to about 0.09, from about 0.005 to about 0.09, from about 0.007 to about 0.09, from about 0.009 to about 0.09, from about 0.01 to about 0.09, from about 0.03 to about 0.09, from about 0.05 to about 0.09, from about 0.07 to about 0.09, from about 0.0003 to about 0.07, from about 0.0005 to about 0.07, from about 0.0007 to about 0.07, from about 0.0009 to about 0.07, from about 0.001 to about 0.07, from about 0.003 to about 0.07, from about 0.005 to about 0.07, from about 0.007 to about 0.07, from about 0.009 to about 0.07, from about 0.01 to about 0.07, from about 0.03 to about 0.07, from about 0.05 to about 0.07, from about 0.0003 to about 0.05, from about 0.0005 to about 0.05, from about 0.0007 to about 0.05, from about 0.0009 to about 0.05, from about 0.001 to about 0.05, from about 0.003 to about 0.05, from about 0.005 to about 0.05, from about 0.007 to about 0.05, from about 0.009 to about 0.05, from about 0.01 to about 0.05, from about 0.03 to about 0.05, from about 0.0003 to about 0.03, from about 0.0005 to about 0.03, from about 0.0007 to about 0.03, from about 0.0009 to about 0.03, from about 0.001 to about 0.03, from about 0.003 to about 0.03, from about 0.005 to about 0.03, from about 0.007 to about 0.03, from about 0.009 to about 0.03, from about 0.01 to about 0.03, from about 0.0003 to about 0.01, from about 0.0005 to about 0.01, from about 0.0007 to about 0.01, from about 0.0009 to about 0.01, from about 0.001 to about 0.01, from about 0.003 to about 0.01, from about 0.005 to about 0.01, from about 0.007 to about 0.01, from about 0.009 to about 0.01, from about 0.0003 to about 0.009, from about 0.0005 to about 0.009, from about 0.0007 to about 0.009, from about 0.0009 to about 0.009, from about 0.001 to about 0.009, from about 0.003 to about 0.009, from about 0.005 to about 0.009, from about 0.007 to about 0.009, from about 0.0003 to about 0.007, from about 0.0005 to about 0.007, from about 0.0007 to about 0.007, from about 0.0009 to about 0.007, from about 0.001 to about 0.007, from about 0.003 to about 0.007, from about 0.005 to about 0.007, from about 0.0003 to about 0.005, from about 0.0005 to about 0.005, from about 0.0007 to about 0.005, from about 0.0009 to about 0.005, from about 0.001 to about 0.005, from about 0.003 to about 0.005, from about 0.0003 to about 0.003, from about 0.0005 to about 0.003, from about 0.0007 to about 0.003, from about 0.0009 to about 0.003, from about 0.001 to about 0.003, from about 0.0003 to about 0.001, from about 0.0005 to about 0.001, from about 0.0007 to about 0.001, from about 0.0009 to about 0.001, from about 0.0003 to about 0.0009, from about 0.0005 to about 0.0009, from about 0.0007 to about 0.0009, from about 0.0003 to about 0.0007, from about 0.0005 to about 0.0007, or from about 0.0003 to about 0.0005% (w/w). In some embodiments, the latanoprost is present at about 0.1, 0.09, 0.07, 0.05, 0.03, 0.01, 0.009, 0.007, 0.005, 0.003, 0.001, 0.0009, 0.0007, 0.0005, or 0.0003% (w/w). In some embodiments, the latanoprost is present in an amount of about 0.005% w/w.

As mentioned above the ophthalmic pharmaceutical formulations provided herein may include a vasoconstrictor agent. A vasoconstrictor agent is an agent having a vasoconstriction effect on blood vessels. Vasoconstriction is the narrowing of blood vessels resulting from contraction of the muscular wall of the vessels. Vasoconstriction is a mechanism by which the body regulates and maintains mean arterial pressure. Therefore, vasoconstrictors or vasoconstrictor agents are agents causing a general increase in systemic blood pressure, but at the same time may cause a localized reduction in blood flow. In some embodiments, the vasoconstrictor agent is an alpha adrenergic agonist. An alpha adrenergic agonist is an agent (e.g., drug, compound), which selectively stimulates alpha adrenergic receptors. Alpha adrenergic receptors are G protein-coupled receptors that are bound by noradrenalin and adrenaline. Binding of an agonist to an alpha adrenergic receptor leads to vasoconstriction, which causes a sympathetic response, where the heart rate increases, the pupils dilate and blood flow is being diverted from non-essential organs to the skeletal muscle. A non-limiting example of an alpha adrenergic agonist is brimonidine. Brimonidine refers, in the customary sense, to CAS Registry No. 59803-98-4. In some embodiments, the alpha adrenergic agonist is brimonidine.

In other embodiments, the vasoconstrictor agent is a beta adrenergic antagonist. A beta adrenergic antagonist is an agent (e.g., drug, compound), which blocks the stimulation of beta adrenergic receptors. Stimulation of beta adrenergic receptors induces smooth muscle relaxation, whereas blocking beta adrenergic receptors causes contraction of smooth muscles. Therefore, beta adrenergic antagonists can cause vasoconstriction. Examples of beta adrenergic antagonists are without limitation befunolol, betaxolol, carteolol, levobunolol, metipranolol, timolol, and mepindolol.

In some embodiments, the beta adrenergic antagonist is timolol. In some embodiments, the timolol is timolol maleate. Timolol maleate refers, in the customary sense, to CAS Registry No. 26839-75-8. The chemical name of timolol maleate is (−)-1-tert-butylamino-3-[(4-morpholino-1,2,5-thiodiazol-3yl)oxy]-2-propanol maleate. Timolol maleate has a molecular weight of 432.50 g/mol and is commercially available from Merck as TIMOPTIC®. In other embodiments, the timolol is timolol hemihydrate. In some embodiments, the timolol is present in a sub-therapeutic amount. In some embodiments, the sub-therapeutic amount is an amount less than about 0.25% w/w. In some embodiments, the sub-therapeutic amount is an amount from about 0.0002 to about 0.25, from about 0.0004 to about 0.25, from about 0.0006 to about 0.25, from about 0.0008 to about 0.25, from about 0.001 to about 0.25, from about 0.002 to about 0.25, from about 0.004 to about 0.25, from about 0.006 to about 0.25, from about 0.008 to about 0.25, from about 0.01 to about 0.25, from about 0.02 to about 0.25, from about 0.04 to about 0.25, from about 0.06 to about 0.25, from about 0.08 to about 0.25, from about 0.1 to about 0.25, from about 0.15 to about 0.25, from about 0.20 to about 0.25, from about 0.0002 to about 0.20, from about 0.0004 to about 0.20, from about 0.0006 to about 0.20, from about 0.0008 to about 0.20, from about 0.001 to about 0.20, from about 0.002 to about 0.20, from about 0.004 to about 0.20, from about 0.006 to about 0.20, from about 0.008 to about 0.20, from about 0.01 to about 0.20, from about 0.02 to about 0.20, from about 0.04 to about 0.20, from about 0.06 to about 0.20, from about 0.08 to about 0.20, from about 0.1 to about 0.20, from about 0.15 to about 0.20, from about 0.0002 to about 0.015, from about 0.0004 to about 0.015, from about 0.0006 to about 0.015, from about 0.0008 to about 0.015, from about 0.001 to about 0.015, from about 0.002 to about 0.015, from about 0.004 to about 0.015, from about 0.006 to about 0.015, from about 0.008 to about 0.015, from about 0.01 to about 0.15, from about 0.02 to about 0.15, from about 0.04 to about 0.15, from about 0.06 to about 0.15, from about 0.08 to about 0.15, from about 0.1 to about 0.15, from about 0.0002 to about 0.001, from about 0.0004 to about 0.001, from about 0.0006 to about 0.001, from about 0.0008 to about 0.001, from about 0.001 to about 0.01, from about 0.002 to about 0.01, from about 0.004 to about 0.01, from about 0.006 to about 0.01, from about 0.008 to about 0.01, from about 0.01 to about 0.1, from about 0.02 to about 0.1, from about 0.04 to about 0.1, from about 0.06 to about 0.1, from about 0.08 to about 0.1, from about 0.0002 to about 0.08, from about 0.0004 to about 0.08, from about 0.0006 to about 0.08, from about 0.0008 to about 0.08, from about 0.001 to about 0.08, from about 0.002 to about 0.08, from about 0.004 to about 0.08, from about 0.006 to about 0.08, from about 0.008 to about 0.08, from about 0.01 to about 0.08, from about 0.02 to about 0.08, from about 0.04 to about 0.08, from about 0.06 to about 0.08, from about 0.0002 to about 0.06, from about 0.0004 to about 0.06, from about 0.0006 to about 0.06, from about 0.0008 to about 0.06, from about 0.001 to about 0.06, from about 0.002 to about 0.06, from about 0.004 to about 0.06, from about 0.006 to about 0.06, from about 0.008 to about 0.06, from about 0.01 to about 0.06, from about 0.02 to about 0.06, from about 0.04 to about 0.06, from about 0.0002 to about 0.04, from about 0.0004 to about 0.04, from about 0.0006 to about 0.04, from about 0.0008 to about 0.04, from about 0.001 to about 0.04, from about 0.002 to about 0.04, from about 0.004 to about 0.04, from about 0.006 to about 0.04, from about 0.008 to about 0.04, from about 0.01 to about 0.04, from about 0.02 to about 0.04, from about 0.0002 to about 0.02, from about 0.0004 to about 0.02, from about 0.0006 to about 0.02, from about 0.0008 to about 0.02, from about 0.001 to about 0.02, from about 0.002 to about 0.02, from about 0.004 to about 0.02, from about 0.006 to about 0.02, from about 0.008 to about 0.02, from about 0.01 to about 0.02, from about 0.0002 to about 0.01, from about 0.0004 to about 0.01, from about 0.0006 to about 0.01, from about 0.0008 to about 0.01, from about 0.001 to about 0.01, from about 0.002 to about 0.01, from about 0.004 to about 0.01, from about 0.006 to about 0.01, from about 0.008 to about 0.01, from about 0.0002 to about 0.008, from about 0.0004 to about 0.008, from about 0.0006 to about 0.008, from about 0.0008 to about 0.008, from about 0.001 to about 0.008, from about 0.002 to about 0.008, from about 0.004 to about 0.008, from about 0.006 to about 0.008, from about 0.0002 to about 0.006, from about 0.0004 to about 0.006, from about 0.0006 to about 0.006, from about 0.0008 to about 0.006, from about 0.001 to about 0.006, from about 0.002 to about 0.006, from about 0.004 to about 0.006, from about 0.0002 to about 0.004, from about 0.0004 to about 0.004, from about 0.0006 to about 0.004, from about 0.0008 to about 0.004, from about 0.001 to about 0.004, from about 0.002 to about 0.004, from about 0.0002 to about 0.002, from about 0.0004 to about 0.002, from about 0.0006 to about 0.002, from about 0.0008 to about 0.002, from about 0.001 to about 0.002, from about 0.0002 to about 0.001, from about 0.0004 to about 0.001, from about 0.0006 to about 0.001, from about 0.0008 to about 0.001, from about 0.0002 to about 0.0008, from about 0.0004 to about 0.0008, from about 0.0006 to about 0.0008, from about 0.0002 to about 0.0006, from about 0.0004 to about 0.0006, or from about 0.0002 to about 0.0004% (w/w). In other embodiments, the sub-therapeutic amount is an amount of about 0.0002, 0.0004, 0.0006, 0.0008, 0.001, 0.002, 0.004, 0.006, 0.008, 0.01, 0.02, 0.04, 0.06, 0.08, 0.1, 0.15, 0.20, or 0.25% (w/w).

In other embodiments, beta adrenergic antagonist is betaxolol. In some embodiments, the betaxolol is present in a sub-therapeutic amount. Betaxolol refers, in the customary sense, to CAS Registry No. 63659-18-7. In some embodiments, the sub-therapeutic amount is an amount less than about 0.25% w/w. In some embodiments, the sub-therapeutic amount is an amount from about 0.0002 to about 0.25, from about 0.0004 to about 0.25, from about 0.0006 to about 0.25, from about 0.0008 to about 0.25, from about 0.001 to about 0.25, from about 0.002 to about 0.25, from about 0.004 to about 0.25, from about 0.006 to about 0.25, from about 0.008 to about 0.25, from about 0.01 to about 0.25, from about 0.02 to about 0.25, from about 0.04 to about 0.25, from about 0.06 to about 0.25, from about 0.08 to about 0.25, from about 0.1 to about 0.25, from about 0.15 to about 0.25, from about 0.20 to about 0.25, from about 0.0002 to about 0.20, from about 0.0004 to about 0.20, from about 0.0006 to about 0.20, from about 0.0008 to about 0.20, from about 0.001 to about 0.20, from about 0.002 to about 0.20, from about 0.004 to about 0.20, from about 0.006 to about 0.20, from about 0.008 to about 0.20, from about 0.01 to about 0.20, from about 0.02 to about 0.20, from about 0.04 to about 0.20, from about 0.06 to about 0.20, from about 0.08 to about 0.20, from about 0.1 to about 0.20, from about 0.15 to about 0.20, from about 0.0002 to about 0.15, from about 0.0004 to about 0.15, from about 0.0006 to about 0.15, from about 0.0008 to about 0.15, from about 0.001 to about 0.15, from about 0.002 to about 0.15, from about 0.004 to about 0.15, from about 0.006 to about 0.15, from about 0.008 to about 0.15, from about 0.01 to about 0.15, from about 0.02 to about 0.15, from about 0.04 to about 0.15, from about 0.06 to about 0.15, from about 0.08 to about 0.15, from about 0.1 to about 0.15, from about 0.0002 to about 0.1, from about 0.0004 to about 0.1, from about 0.0006 to about 0.1, from about 0.0008 to about 0.1, from about 0.001 to about 0.1, from about 0.002 to about 0.1, from about 0.004 to about 0.1, from about 0.006 to about 0.1, from about 0.008 to about 0.1, from about 0.01 to about 0.1, from about 0.02 to about 0.1, from about 0.04 to about 0.1, from about 0.06 to about 0.1, from about 0.08 to about 0.1, from about 0.0002 to about 0.08, from about 0.0004 to about 0.08, from about 0.0006 to about 0.08, from about 0.0008 to about 0.08, from about 0.001 to about 0.08, from about 0.002 to about 0.08, from about 0.004 to about 0.08, from about 0.006 to about 0.08, from about 0.008 to about 0.08, from about 0.01 to about 0.08, from about 0.02 to about 0.08, from about 0.04 to about 0.08, from about 0.06 to about 0.08, from about 0.0002 to about 0.06, from about 0.0004 to about 0.06, from about 0.0006 to about 0.06, from about 0.0008 to about 0.06, from about 0.001 to about 0.06, from about 0.002 to about 0.06, from about 0.004 to about 0.06, from about 0.006 to about 0.06, from about 0.008 to about 0.06, from about 0.01 to about 0.06, from about 0.02 to about 0.06, from about 0.04 to about 0.06, from about 0.0002 to about 0.04, from about 0.0004 to about 0.04, from about 0.0006 to about 0.04, from about 0.0008 to about 0.04, from about 0.001 to about 0.04, from about 0.002 to about 0.04, from about 0.004 to about 0.04, from about 0.006 to about 0.04, from about 0.008 to about 0.04, from about 0.01 to about 0.04, from about 0.02 to about 0.04, from about 0.0002 to about 0.02, from about 0.0004 to about 0.02, from about 0.0006 to about 0.02, from about 0.0008 to about 0.02, from about 0.001 to about 0.02, from about 0.002 to about 0.02, from about 0.004 to about 0.02, from about 0.006 to about 0.02, from about 0.008 to about 0.02, from about 0.01 to about 0.02, from about 0.0002 to about 0.01, from about 0.0004 to about 0.01, from about 0.0006 to about 0.01, from about 0.0008 to about 0.01, from about 0.001 to about 0.01, from about 0.002 to about 0.01, from about 0.004 to about 0.01, from about 0.006 to about 0.01, from about 0.008 to about 0.01, from about 0.0002 to about 0.008, from about 0.0004 to about 0.008, from about 0.0006 to about 0.008, from about 0.0008 to about 0.008, from about 0.001 to about 0.008, from about 0.002 to about 0.008, from about 0.004 to about 0.008, from about 0.006 to about 0.008, from about 0.0002 to about 0.006, from about 0.0004 to about 0.006, from about 0.0006 to about 0.006, from about 0.0008 to about 0.006, from about 0.001 to about 0.006, from about 0.002 to about 0.006, from about 0.004 to about 0.006, from about 0.0002 to about 0.004, from about 0.0004 to about 0.004, from about 0.0006 to about 0.004, from about 0.0008 to about 0.004, from about 0.001 to about 0.004, from about 0.002 to about 0.004, from about 0.0002 to about 0.002, from about 0.0004 to about 0.002, from about 0.0006 to about 0.002, from about 0.0008 to about 0.002, from about 0.001 to about 0.002, from about 0.0002 to about 0.001, from about 0.0004 to about 0.001, from about 0.0006 to about 0.001, from about 0.0008 to about 0.001, from about 0.0002 to about 0.0008, from about 0.0004 to about 0.0008, from about 0.0006 to about 0.0008, from about 0.0002 to about 0.0006, from about 0.0004 to about 0.0006, or from about 0.0002 to about 0.0004% (w/w). In other embodiments, the sub-therapeutic amount is an amount of about 0.0002, 0.0004, 0.0006, 0.0008, 0.001, 0.002, 0.004, 0.006, 0.008, 0.01, 0.02, 0.04, 0.06, 0.08, 0.1, 0.15, 0.20, or 0.25% (w/w). In some embodiments, the betaxolol is a betaxolol salt.

In other embodiments, the beta adrenergic antagonist is levobunolol. Levobunolol refers, in the customary sense, to CAS Registry No. 47141-42-4. In some embodiments, the levobunolol is present in a sub-therapeutic amount. In some embodiments, the sub-therapeutic amount is an amount less than about 0.25% w/w. In some embodiments, the sub-therapeutic amount is an amount from about 0.0002 to about 0.25, from about 0.0004 to about 0.25, from about 0.0006 to about 0.25, from about 0.0008 to about 0.25, from about 0.001 to about 0.25, from about 0.002 to about 0.25, from about 0.004 to about 0.25, from about 0.006 to about 0.25, from about 0.008 to about 0.25, from about 0.01 to about 0.25, from about 0.02 to about 0.25, from about 0.04 to about 0.25, from about 0.06 to about 0.25, from about 0.08 to about 0.25, from about 0.1 to about 0.25, from about 0.15 to about 0.25, from about 0.20 to about 0.25, from about 0.0002 to about 0.20, from about 0.0004 to about 0.20, from about 0.0006 to about 0.20, from about 0.0008 to about 0.20, from about 0.001 to about 0.20, from about 0.002 to about 0.20, from about 0.004 to about 0.20, from about 0.006 to about 0.20, from about 0.008 to about 0.20, from about 0.01 to about 0.20, from about 0.02 to about 0.20, from about 0.04 to about 0.20, from about 0.06 to about 0.20, from about 0.08 to about 0.20, from about 0.1 to about 0.20, from about 0.15 to about 0.20, from about 0.0002 to about 0.15, from about 0.0004 to about 0.15, from about 0.0006 to about 0.15, from about 0.0008 to about 0.15, from about 0.001 to about 0.15, from about 0.002 to about 0.15, from about 0.004 to about 0.15, from about 0.006 to about 0.15, from about 0.008 to about 0.15, from about 0.01 to about 0.15, from about 0.02 to about 0.15, from about 0.04 to about 0.15, from about 0.06 to about 0.15, from about 0.08 to about 0.15, from about 0.1 to about 0.15, from about 0.0002 to about 0.1, from about 0.0004 to about 0.1, from about 0.0006 to about 0.1, from about 0.0008 to about 0.1, from about 0.001 to about 0.1, from about 0.002 to about 0.1, from about 0.004 to about 0.1, from about 0.006 to about 0.1, from about 0.008 to about 0.1, from about 0.01 to about 0.1, from about 0.02 to about 0.1, from about 0.04 to about 0.1, from about 0.06 to about 0.1, from about 0.08 to about 0.1, from about 0.0002 to about 0.08, from about 0.0004 to about 0.08, from about 0.0006 to about 0.08, from about 0.0008 to about 0.08, from about 0.001 to about 0.08, from about 0.002 to about 0.08, from about 0.004 to about 0.08, from about 0.006 to about 0.08, from about 0.008 to about 0.08, from about 0.01 to about 0.08, from about 0.02 to about 0.08, from about 0.04 to about 0.08, from about 0.06 to about 0.08, from about 0.0002 to about 0.06, from about 0.0004 to about 0.06, from about 0.0006 to about 0.06, from about 0.0008 to about 0.06, from about 0.001 to about 0.06, from about 0.002 to about 0.06, from about 0.004 to about 0.06, from about 0.006 to about 0.06, from about 0.008 to about 0.06, from about 0.01 to about 0.06, from about 0.02 to about 0.06, from about 0.04 to about 0.06, from about 0.0002 to about 0.04, from about 0.0004 to about 0.04, from about 0.0006 to about 0.04, from about 0.0008 to about 0.04, from about 0.001 to about 0.04, from about 0.002 to about 0.04, from about 0.004 to about 0.04, from about 0.006 to about 0.04, from about 0.008 to about 0.04, from about 0.01 to about 0.04, from about 0.02 to about 0.04, from about 0.0002 to about 0.02, from about 0.0004 to about 0.02, from about 0.0006 to about 0.02, from about 0.0008 to about 0.02, from about 0.001 to about 0.02, from about 0.002 to about 0.02, from about 0.004 to about 0.02, from about 0.006 to about 0.02, from about 0.008 to about 0.02, from about 0.01 to about 0.02, from about 0.0002 to about 0.01, from about 0.0004 to about 0.01, from about 0.0006 to about 0.01, from about 0.0008 to about 0.01, from about 0.001 to about 0.01, from about 0.002 to about 0.01, from about 0.004 to about 0.01, from about 0.006 to about 0.01, from about 0.008 to about 0.01, from about 0.0002 to about 0.008, from about 0.0004 to about 0.008, from about 0.0006 to about 0.008, from about 0.0008 to about 0.008, from about 0.001 to about 0.008, from about 0.002 to about 0.008, from about 0.004 to about 0.008, from about 0.006 to about 0.008, from about 0.0002 to about 0.006, from about 0.0004 to about 0.006, from about 0.0006 to about 0.006, from about 0.0008 to about 0.006, from about 0.001 to about 0.006, from about 0.002 to about 0.006, from about 0.004 to about 0.006, from about 0.0002 to about 0.004, from about 0.0004 to about 0.004, from about 0.0006 to about 0.004, from about 0.0008 to about 0.004, from about 0.001 to about 0.004, from about 0.002 to about 0.004, from about 0.0002 to about 0.002, from about 0.0004 to about 0.002, from about 0.0006 to about 0.002, from about 0.0008 to about 0.002, from about 0.001 to about 0.002, from about 0.0002 to about 0.001, from about 0.0004 to about 0.001, from about 0.0006 to about 0.001, from about 0.0008 to about 0.001, from about 0.0002 to about 0.0008, from about 0.0004 to about 0.0008, from about 0.0006 to about 0.0008, from about 0.0002 to about 0.0006, from about 0.0004 to about 0.0006, or from about 0.0002 to about 0.0004% (w/w). In other embodiments, the sub-therapeutic amount is an amount of about 0.0002, 0.0004, 0.0006, 0.0008, 0.001, 0.002, 0.004, 0.006, 0.008, 0.01, 0.02, 0.04, 0.06, 0.08, 0.1, 0.15, 0.20, or 0.25% (w/w). In some embodiments, the levobunolol is a levobunolol salt.

In other embodiments, the beta adrenergic antagonist is metipranolol. Metipranolol refers, in the customary sense, to CAS Registry No. 22664-55-7. In some embodiments, the metipranolol is present in a sub-therapeutic amount. In some embodiments, the sub-therapeutic amount is an amount less than about 0.3% w/w. In some embodiments, the sub-therapeutic amount is an amount from about 0.003 to about 0.3, from about 0.004 to about 0.3, from about 0.006 to about 0.3, from about 0.008 to about 0.3, from about 0.01 to about 0.3, from about 0.03 to about 0.3, from about 0.04 to about 0.3, from about 0.06 to about 0.3, from about 0.08 to about 0.3, from about 0.1 to about 0.3, from about 0.15 to about 0.3, from about 0.20 to about 0.3, from about 0.25 to about 0.3, from about 0.003 to about 0.25, from about 0.004 to about 0.25, from about 0.006 to about 0.25, from about 0.008 to about 0.25, from about 0.01 to about 0.25, from about 0.03 to about 0.25, from about 0.04 to about 0.25, from about 0.06 to about 0.25, from about 0.08 to about 0.25, from about 0.1 to about 0.25, from about 0.15 to about 0.25, from about 0.20 to about 0.25, from about 0.003 to about 0.20, from about 0.004 to about 0.20, from about 0.006 to about 0.20, from about 0.008 to about 0.20, from about 0.01 to about 0.20, from about 0.03 to about 0.20, from about 0.04 to about 0.20, from about 0.06 to about 0.20, from about 0.08 to about 0.20, from about 0.1 to about 0.20, from about 0.15 to about 0.20, from about 0.003 to about 0.15, from about 0.004 to about 0.15, from about 0.006 to about 0.15, from about 0.008 to about 0.15, from about 0.01 to about 0.15, from about 0.03 to about 0.15, from about 0.04 to about 0.15, from about 0.06 to about 0.15, from about 0.08 to about 0.15, from about 0.1 to about 0.15, from about 0.003 to about 0.1, from about 0.004 to about 0.1, from about 0.006 to about 0.1, from about 0.008 to about 0.1, from about 0.01 to about 0.1, from about 0.03 to about 0.1, from about 0.04 to about 0.1, from about 0.06 to about 0.1, from about 0.08 to about 0.1, from about 0.003 to about 0.08, from about 0.004 to about 0.08, from about 0.006 to about 0.08, from about 0.008 to about 0.08, from about 0.01 to about 0.08, from about 0.03 to about 0.08, from about 0.04 to about 0.08, from about 0.06 to about 0.08, from about 0.003 to about 0.06, from about 0.004 to about 0.06, from about 0.006 to about 0.06, from about 0.008 to about 0.06, from about 0.01 to about 0.06, from about 0.03 to about 0.06, from about 0.04 to about 0.06, from about 0.003 to about 0.04, from about 0.004 to about 0.04, from about 0.006 to about 0.04, from about 0.008 to about 0.04, from about 0.01 to about 0.04, from about 0.03 to about 0.04, from about 0.003 to about 0.03, from about 0.004 to about 0.03, from about 0.006 to about 0.03, from about 0.008 to about 0.03, from about 0.01 to about 0.03, from about 0.003 to about 0.01, from about 0.004 to about 0.01, from about 0.006 to about 0.01, from about 0.008 to about 0.01, from about 0.003 to about 0.008, from about 0.004 to about 0.008, from about 0.006 to about 0.008, from about 0.003 to about 0.006, from about 0.004 to about 0.006, or from about 0.003 to about 0.004% (w/w). In other embodiments, the sub-therapeutic amount is an amount of about 0.3, 0.25, 0.20, 0.15, 0.1, 0.08, 0.06, 0.04, 0.03, 0.01, 0.008, 0.006, 0.004, or 0.003% (w/w). In some embodiments, the metipranolol is a metipranolol salt.

The compositions and products according to the embodiments of the present invention may include a buffering agent, a tonicity agent, a salt, a thickening agent or a preservative. In some embodiments, the composition includes a buffering agent, a tonicity agent, a salt, a thickening agent and a preservative.

A buffering agents are means for adjusting the pH of the compositions provided to be an ophthalmically acceptable pH (e.g. neutral pH). Buffers appropriate to for the compositions provided include acetate buffers, citrate buffers, phosphate buffers and borate buffers. Acids or bases may also be used to adjust the pH of the ophthalmic formulations as needed. The pH of the disclosed compositions should preferably be maintained between 6.5 and 7.2 with an appropriate buffering agent.

The term "tonicity agent" as used herein refers to a compound or ion useful for adjusting the osmotic pressure or tension of a solution, often relative to that of blood. Examples for tonicity agents are without limitation, glycerin, erythritol, mannitol, potassium, chloride, and sodium chloride. In some embodiments, the tonicity agent is glycerin. In some further embodiments, the tonicity agent is present from about 0.5% w/w to about 6% w/w.

The formulation's viscosity is a factor that determines how well the formulation sticks to the skin or ophthalmic tissue or does not run off the skin or ophthalmic tissue when applied. The viscosity of the formulation can be optimized using one or more pharmaceutically acceptable thickening agents that do not significantly interact with the components of the formulation, do not significantly reduce flux of the formulation, and do not cause stinging or irritation. Non-limiting examples of suitable thickeners useful herein include cellulosic polymers, such as gum arabic, gum acacia, gum tragacanth, locust bean gum, guar gum, hydroxypropyl guar, xanthan gum, talc, cellulose gum, sclerotium gum, carageenan gum, karaya gum, cellulose gum, rosin, methylcellulose, hydroxyethylcellulose, hydroxypropylcellulose, hydroxymethylcellulose, hydroxypropylmethylcellulose, methylhydroxyethylcellulose, cetyl hydroxyethylcellulose, carboxymethylcellulose, corn starch, hydroxypropyl starch phosphate, distarch phosphate, distarch dimethylene urea, aluminum starch octenyl succinate, maltodextrin, dextran, poly(acrylamide), PEG-150 distearate, PEG-150/decyl alcohol/SMDI copolymer, PEG-150/stearyl alcohol/SMDI copolymer, PEG-180/Laureth-50/TMMG copolymer, Polyether 1, acrylic acid/acrylamidomethyl propane sulfonic acid copolymer, acrylate/C10-30 alkyl acrylate cross polymer, acrylate/beheneth-25 methacrylate copolymer, acrylate/steareth-20 methacrylate copolymer, acrylate/steareth-20 copolymer, acrylate/VA cross polymer, acrylic acid/acrylonitrogen copolymer, ammonium acryloyldimethyltaurate/beheneth-25 methacrylate copolymer, ammonium acryloyldimethyltaurate/VP copolymer, caprylic/capric triglyceride (and) sodium acrylate copolymer, PVM/MA decadiene cross polymer, alginic acid, propylene glycol alginate, dimethicone, silica dimethyl silylate, a dimethylacrylamide/acrylic acid/polystyrene ethyl methacrylate copolymer, derivatives thereof, and mixtures thereof.

Preservatives that can be used in the ophthalmic pharmaceutical formulations of the present embodiments include, but are not limited to, benzalkonium chloride, chlorobutanol, thimerosal, phenylmercuric acetate and phenylmercuric nitrate. Preservative-free compositions can be considered, for example for patients experiencing hypersensitivity reactions with the above listed preservatives or other preservatives not listed. Thus, in some embodiments, the composition further includes a buffering agent, a tonicity agent, a salt and a thickening agent.

In some embodiments, the composition consists essentially of bimatoprost, timolol, a buffering agent, a tonicity agent, a salt, a thickening agent and a preservative. Where the composition consists essentially of bimatoprost, timolol, a buffering agent, a tonicity agent, a salt, a thickening agent and a preservative, the composition consists of bimatoprost and timolol, and any appropriate buffering agent, tonicity agent, salt, thickening agent and preservative. In some embodiments, the timolol is present in a sub-therapeutic amount. As described earlier the sub-therapeutic amount may be an amount less than about 0.25% w/w. Thus, in some embodiments, the sub-therapeutic amount is an amount of about 0.0002, 0.0004, 0.0006, 0.0008, 0.001, 0.002, 0.004, 0.006, 0.008, 0.01, 0.02, 0.04, 0.06, 0.08, 0.1, 0.15, 0.20, or 0.25% (w/w).

The compositions provided herein may consist essentially of bimatoprost, a beta adrenergic antagonist, buffering agent, a tonicity agent, a salt, a thickening agent and a preservative.

Where the compositions provided herein may consist essentially of bimatoprost, a beta adrenergic antagonist, buffering agent, a tonicity agent, a salt, a thickening agent and a preservative, the composition consists of bimatoprost and a beta adrenergic antagonist, and any appropriate buffering agent, tonicity agent, salt, thickening agent and preservative. In some embodiments, the beta adrenergic antagonist is present in a sub-therapeutic amount. Non-limiting examples of a beta adrenergic compound suitable for the compositions and methods according to the embodiments of the present invention are betaxolol, levobunolol, or metipranolol. Thus, in some embodiments, the composition consists essentially of bimatoprost, betaxolol, a buffering agent, a tonicity agent, a salt, a preservative and a thickening agent. In some further embodiments, the betaxolol is present in a sub-therapeutic amount. In further embodiments, the sub-therapeutic amount is an amount less than about 0.25% w/w.

In other embodiments, the composition consists essentially of bimatoprost, levobunolol, a buffering agent, a tonicity agent, a salt, a preservative and a thickening agent. In further embodiments, the levobunolol is present in a sub-therapeutic amount. In some further embodiment, the sub-therapeutic amount is an amount less than about 0.25% w/w.

In some embodiments, the composition consists essentially of bimatoprost, metipranolol, a buffering agent, a tonicity agent, a salt, a preservative and a thickening agent. In further embodiments, the metipranolol is present in a sub-therapeutic amount. In some further embodiment, the sub-therapeutic amount is an amount less than about 0.3% w/w.

Tables 1-12 describe various examples of combinations of effective amounts of the prostaglandin agent (e.g., bimatoprost, travoprost, latanoprost) and the vasoconstrictor agent (e.g., timolol, betaxolol, levobunolol, metipranolol, tetrahydrozoline hydrochloride, brimonidine etc.). In particular, Table 1 provides 342 different combination embodiments of bimatoprost, as shown in the first column labeled "Bimatoprost % w/w", and timolol, as shown in the first row labeled "Timolol % w/w." Specific concentrations of bimatoprost and timolol for each of the combination embodiments described in Table 1 and numbered from 1 to 19 are shown, respectively, in the cells in the first row, which correspond to the numbered cell.

Table 2 provides 342 different combination embodiments of bimatoprost, as shown in the first column labeled "Bimatoprost % w/w", and betaxolol as shown in the first row labeled "Betaxolol % w/w." Specific concentrations of bimatoprost and betaxolol for each of the combination embodiments described in Table 2 and numbered from 343 to 361 are shown, respectively, in the cells in the first row, which correspond to the numbered cell.

Table 3 provides 342 different combination embodiments of bimatoprost, as shown in the first column labeled "Bimatoprost % w/w", and levobunolol as shown in the first row labeled "Levobunolol % w/w." Specific concentrations of bimatoprost and levobunolol for each of the combination embodiments described in Table 3 and numbered from 685 to 703 are shown, respectively, in the cells in the first row, which correspond to the numbered cell.

Table 4 provides 266 different combination embodiments of bimatoprost, as shown in the first column labeled "Bimatoprost % w/w", and metipranolol as shown in the first row labeled "Metipranolol % w/w." Specific concentrations of bimatoprost and metipranolol for each of the combination embodiments described in Table 4 and numbered from 1027 to 1045 are shown, respectively, in the cells in the first row, which correspond to the numbered cell.

Table 5 provides 270 different combination embodiments of travoprost, as shown in the first column labeled "Travoprost % w/w", and timolol, as shown in the first row labeled "Timolol % w/w." Specific concentrations of travoprost and timolol for each of the combination embodiments described in Table 5 and numbered from 1293 to 1307 are shown, respectively, in the cells in the first row, which correspond to the numbered cell.

Table 6 provides 270 different combination embodiments of travoprost, as shown in the first column labeled "Travoprost % w/w", and betaxolol as shown in the first row labeled "Betaxolol % w/w." Specific concentrations of travoprost and betaxolol for each of the combination embodiments described in Table 6 and numbered from 1563 to 1577 are shown, respectively, in the cells in the first row, which correspond to the numbered cell.

Table 7 provides 270 different combination embodiments of travoprost, as shown in the first column labeled "Travoprost % w/w", and levobunolol as shown in the first row labeled "Levobunolol % w/w." Specific concentrations of travoprost and levobunolol for each of the combination embodiments described in Table 7 and numbered from 1833 to 1847 are shown, respectively, in the cells in the first row, which correspond to the numbered cell.

Table 8 provides 210 different combination embodiments of travoprost, as shown in the first column labeled "Travoprost % w/w", and metipranolol as shown in the first row labeled "Metipranolol % w/w." Specific concentrations of travoprost and metipranolol for each of the combination embodiments described in Table 8 and numbered from 2103 to 2117 are shown, respectively, in the cells in the first row, which correspond to the numbered cell.

Table 9 provides 270 different combination embodiments of latanoprost, as shown in the first column labeled "Latanoprost % w/w", and timolol, as shown in the first row labeled "Timolol % w/w." Specific concentrations of latanoprost and timolol for each of the combination embodiments described in Table 9 and numbered from 2313 to 2327 are shown, respectively, in the cells in the first row, which correspond to the numbered cell.

Table 10 provides 270 different combination embodiments of latanoprost, as shown in the first column labeled "Latanoprost % w/w", and betaxolol as shown in the first row labeled "Betaxolol % w/w." Specific concentrations of latanoprost and betaxolol for each of the combination embodiments described in Table 10 and numbered from 2583 to 2597 are shown, respectively, in the cells in the first row, which correspond to the numbered cell.

Table 11 provides 270 different combination embodiments of latanoprost, as shown in the first column labeled "Latanoprost % w/w", and levobunolol as shown in the first row labeled "Levobunolol % w/w." Specific concentrations of latanoprost and levobunolol for each of the combination embodiments described in Table 11 and numbered from 2853 to 2867 are shown, respectively, in the cells in the first row, which correspond to the numbered cell.

Table 12 provides 210 different combination embodiments of latanoprost, as shown in the first column labeled "Latanoprost % w/w", and metipranolol as shown in the first row labeled "Metipranolol % w/w." Specific concentrations of latanoprost and metipranolol for each of the combination embodiments described in Table 12 and numbered from 3123 to 3137 are shown, respectively, in the cells in the first row, which correspond to the numbered cell.

TABLE 1

Effective Amounts of Bimatoprost and Timolol

| Bimatoprost % w/w | Timolol % w/w | | | | | | | | | |
|---|---|---|---|---|---|---|---|---|---|---|
| | 0.0002 | 0.0004 | 0.0006 | 0.0008 | 0.0010 | 0.0020 | 0.0040 | 0.0060 | 0.0080 | 0.0100 |
| 0.001 | 1 | 20 | 39 | 58 | 77 | 96 | 115 | 134 | 153 | 172 |
| 0.002 | 2 | 21 | 40 | 59 | 78 | 97 | 116 | 135 | 154 | 173 |
| 0.003 | 3 | 22 | 41 | 60 | 79 | 98 | 117 | 136 | 155 | 174 |
| 0.004 | 4 | 23 | 42 | 61 | 80 | 99 | 118 | 137 | 156 | 175 |
| 0.005 | 5 | 24 | 43 | 62 | 81 | 100 | 119 | 138 | 157 | 176 |
| 0.006 | 6 | 25 | 44 | 63 | 82 | 101 | 120 | 139 | 158 | 177 |
| 0.007 | 7 | 26 | 45 | 64 | 83 | 102 | 121 | 140 | 159 | 178 |
| 0.008 | 8 | 27 | 46 | 65 | 84 | 103 | 122 | 141 | 160 | 179 |
| 0.009 | 9 | 28 | 47 | 66 | 85 | 104 | 123 | 142 | 161 | 180 |
| 0.010 | 10 | 29 | 48 | 67 | 86 | 105 | 124 | 143 | 162 | 181 |
| 0.020 | 11 | 30 | 49 | 68 | 87 | 106 | 125 | 144 | 163 | 182 |
| 0.030 | 12 | 31 | 50 | 69 | 88 | 107 | 126 | 145 | 164 | 183 |
| 0.040 | 13 | 32 | 51 | 70 | 89 | 108 | 127 | 146 | 165 | 184 |
| 0.050 | 14 | 33 | 52 | 71 | 90 | 109 | 128 | 147 | 166 | 185 |
| 0.060 | 15 | 34 | 53 | 72 | 91 | 110 | 129 | 148 | 167 | 186 |
| 0.070 | 16 | 35 | 54 | 73 | 92 | 111 | 130 | 149 | 168 | 187 |
| 0.080 | 17 | 36 | 55 | 74 | 93 | 112 | 131 | 150 | 169 | 188 |
| 0.090 | 18 | 37 | 56 | 75 | 94 | 113 | 132 | 151 | 170 | 189 |
| 0.100 | 19 | 38 | 57 | 76 | 95 | 114 | 133 | 152 | 171 | 190 |

| Bimatoprost % w/w | Timolol % w/w | | | | | | | |
|---|---|---|---|---|---|---|---|---|
| | 0.0200 | 0.0400 | 0.0600 | 0.0800 | 0.10 | 0.15 | 0.20 | 0.25 |
| 0.001 | 191 | 210 | 229 | 248 | 267 | 286 | 305 | 324 |
| 0.002 | 192 | 211 | 230 | 249 | 268 | 287 | 306 | 325 |
| 0.003 | 193 | 212 | 231 | 250 | 269 | 288 | 307 | 326 |
| 0.004 | 194 | 213 | 232 | 251 | 270 | 289 | 308 | 327 |
| 0.005 | 195 | 214 | 233 | 252 | 271 | 290 | 309 | 328 |
| 0.006 | 196 | 215 | 234 | 253 | 272 | 291 | 310 | 329 |
| 0.007 | 197 | 216 | 235 | 254 | 273 | 292 | 311 | 330 |
| 0.008 | 198 | 217 | 236 | 255 | 274 | 293 | 312 | 331 |
| 0.009 | 199 | 218 | 237 | 256 | 275 | 294 | 313 | 332 |
| 0.010 | 200 | 219 | 238 | 257 | 276 | 295 | 314 | 333 |
| 0.020 | 201 | 220 | 239 | 258 | 277 | 296 | 315 | 334 |
| 0.030 | 202 | 221 | 240 | 259 | 278 | 297 | 316 | 335 |
| 0.040 | 203 | 222 | 241 | 260 | 279 | 298 | 317 | 336 |
| 0.050 | 204 | 223 | 242 | 261 | 280 | 299 | 318 | 337 |
| 0.060 | 205 | 224 | 243 | 262 | 281 | 300 | 319 | 338 |
| 0.070 | 206 | 225 | 244 | 263 | 282 | 301 | 320 | 339 |
| 0.080 | 207 | 226 | 245 | 264 | 283 | 302 | 321 | 340 |
| 0.090 | 208 | 227 | 246 | 265 | 284 | 303 | 322 | 341 |
| 0.100 | 209 | 228 | 247 | 266 | 285 | 304 | 323 | 342 |

TABLE 2

Effective Amounts of Bimatoprost and Betaxolol

| Bimatoprost % w/w | Betaxolol % w/w | | | | | | | | |
|---|---|---|---|---|---|---|---|---|---|
| | 0.0002 | 0.0004 | 0.0006 | 0.0008 | 0.0010 | 0.0020 | 0.0040 | 0.0060 | 0.0080 |
| 0.001 | 343 | 362 | 381 | 400 | 419 | 438 | 457 | 476 | 495 |
| 0.002 | 344 | 363 | 382 | 401 | 420 | 439 | 458 | 477 | 496 |
| 0.003 | 345 | 364 | 383 | 402 | 421 | 440 | 459 | 478 | 497 |
| 0.004 | 346 | 365 | 384 | 403 | 422 | 441 | 460 | 479 | 498 |
| 0.005 | 347 | 366 | 385 | 404 | 423 | 442 | 461 | 480 | 499 |
| 0.006 | 348 | 367 | 386 | 405 | 424 | 443 | 462 | 481 | 500 |
| 0.007 | 349 | 368 | 387 | 406 | 425 | 444 | 463 | 482 | 501 |
| 0.008 | 350 | 369 | 388 | 407 | 426 | 445 | 464 | 483 | 502 |
| 0.009 | 351 | 370 | 389 | 408 | 427 | 446 | 465 | 484 | 503 |
| 0.010 | 352 | 371 | 390 | 409 | 428 | 447 | 466 | 485 | 504 |
| 0.020 | 353 | 372 | 391 | 410 | 429 | 448 | 467 | 486 | 505 |
| 0.030 | 354 | 373 | 392 | 411 | 430 | 449 | 468 | 487 | 506 |
| 0.040 | 355 | 374 | 393 | 412 | 431 | 450 | 469 | 488 | 507 |
| 0.050 | 356 | 375 | 394 | 413 | 432 | 451 | 470 | 489 | 508 |
| 0.060 | 357 | 376 | 395 | 414 | 433 | 452 | 471 | 490 | 509 |
| 0.070 | 358 | 377 | 396 | 415 | 434 | 453 | 472 | 491 | 510 |
| 0.080 | 359 | 378 | 397 | 416 | 435 | 454 | 473 | 492 | 511 |

TABLE 2-continued

Effective Amounts of Bimatoprost and Betaxolol

| 0.090 | 360 | 379 | 398 | 417 | 436 | 455 | 474 | 493 | 512 |
|---|---|---|---|---|---|---|---|---|---|
| 0.100 | 361 | 380 | 399 | 418 | 437 | 456 | 475 | 494 | 513 |

| Bimatoprost | Betaxolol % w/w | | | | | | | | |
|---|---|---|---|---|---|---|---|---|---|
| % w/w | 0.0100 | 0.0200 | 0.0400 | 0.0600 | 0.0800 | 0.10 | 0.15 | 0.20 | 0.25 |
| 0.001 | 514 | 533 | 552 | 571 | 590 | 609 | 628 | 647 | 666 |
| 0.002 | 515 | 534 | 553 | 572 | 591 | 610 | 629 | 648 | 667 |
| 0.003 | 516 | 535 | 554 | 573 | 592 | 611 | 630 | 649 | 668 |
| 0.004 | 517 | 536 | 555 | 574 | 593 | 612 | 631 | 650 | 669 |
| 0.005 | 518 | 537 | 556 | 575 | 594 | 613 | 632 | 651 | 670 |
| 0.006 | 519 | 538 | 557 | 576 | 595 | 614 | 633 | 652 | 671 |
| 0.007 | 520 | 539 | 558 | 577 | 596 | 615 | 634 | 653 | 672 |
| 0.008 | 521 | 540 | 559 | 578 | 597 | 616 | 635 | 654 | 673 |
| 0.009 | 522 | 541 | 560 | 579 | 598 | 617 | 636 | 655 | 674 |
| 0.010 | 523 | 542 | 561 | 580 | 599 | 618 | 637 | 656 | 675 |
| 0.020 | 524 | 543 | 562 | 581 | 600 | 619 | 638 | 657 | 676 |
| 0.030 | 525 | 544 | 563 | 582 | 601 | 620 | 639 | 658 | 677 |
| 0.040 | 526 | 545 | 564 | 583 | 602 | 621 | 640 | 659 | 678 |
| 0.050 | 527 | 546 | 565 | 584 | 603 | 622 | 641 | 660 | 679 |
| 0.060 | 528 | 547 | 566 | 585 | 604 | 623 | 642 | 661 | 680 |
| 0.070 | 529 | 548 | 567 | 586 | 605 | 624 | 643 | 662 | 681 |
| 0.080 | 530 | 549 | 568 | 587 | 606 | 625 | 644 | 663 | 682 |
| 0.090 | 531 | 550 | 569 | 588 | 607 | 626 | 645 | 664 | 683 |
| 0.100 | 532 | 551 | 570 | 589 | 608 | 627 | 646 | 665 | 684 |

TABLE 3

Effective Amounts of Bimatoprost and Levobunolol

| Bimatoprost | Levobunolol % w/w | | | | | | | | |
|---|---|---|---|---|---|---|---|---|---|
| % w/w | 0.0002 | 0.0004 | 0.0006 | 0.0008 | 0.0010 | 0.0020 | 0.0040 | 0.0060 | 0.0080 |
| 0.001 | 685 | 704 | 723 | 742 | 761 | 780 | 799 | 818 | 837 |
| 0.002 | 686 | 705 | 724 | 743 | 762 | 781 | 800 | 819 | 838 |
| 0.003 | 687 | 706 | 725 | 744 | 763 | 782 | 801 | 820 | 839 |
| 0.004 | 688 | 707 | 726 | 745 | 764 | 783 | 802 | 821 | 840 |
| 0.005 | 689 | 708 | 727 | 746 | 765 | 784 | 803 | 822 | 841 |
| 0.006 | 690 | 709 | 728 | 747 | 766 | 785 | 804 | 823 | 842 |
| 0.007 | 691 | 710 | 729 | 748 | 767 | 786 | 805 | 824 | 843 |
| 0.008 | 692 | 711 | 730 | 749 | 768 | 787 | 806 | 825 | 844 |
| 0.009 | 693 | 712 | 731 | 750 | 769 | 788 | 807 | 826 | 845 |
| 0.010 | 694 | 713 | 732 | 751 | 770 | 789 | 808 | 827 | 846 |
| 0.020 | 695 | 714 | 733 | 752 | 771 | 790 | 809 | 828 | 847 |
| 0.030 | 696 | 715 | 734 | 753 | 772 | 791 | 810 | 829 | 848 |
| 0.040 | 697 | 716 | 735 | 754 | 773 | 792 | 811 | 830 | 849 |
| 0.050 | 698 | 717 | 736 | 755 | 774 | 793 | 812 | 831 | 850 |
| 0.060 | 699 | 718 | 737 | 756 | 775 | 794 | 813 | 832 | 851 |
| 0.070 | 700 | 719 | 738 | 757 | 776 | 795 | 814 | 833 | 852 |
| 0.080 | 701 | 720 | 739 | 758 | 777 | 796 | 815 | 834 | 853 |
| 0.090 | 702 | 721 | 740 | 759 | 778 | 797 | 816 | 835 | 854 |
| 0.100 | 703 | 722 | 741 | 760 | 779 | 798 | 817 | 836 | 855 |

| Bimatoprost | Levobunolol % w/w | | | | | | | | |
|---|---|---|---|---|---|---|---|---|---|
| % w/w | 0.01 | 0.02 | 0.04 | 0.06 | 0.08 | 0.10 | 0.15 | 0.20 | 0.25 |
| 0.001 | 856 | 875 | 894 | 913 | 932 | 951 | 970 | 989 | 1008 |
| 0.002 | 857 | 876 | 895 | 914 | 933 | 952 | 971 | 990 | 1009 |
| 0.003 | 858 | 877 | 896 | 915 | 934 | 953 | 972 | 991 | 1010 |
| 0.004 | 859 | 878 | 897 | 916 | 935 | 954 | 973 | 992 | 1011 |
| 0.005 | 860 | 879 | 898 | 917 | 936 | 955 | 974 | 993 | 1012 |
| 0.006 | 861 | 880 | 899 | 918 | 937 | 956 | 975 | 994 | 1013 |
| 0.007 | 862 | 881 | 900 | 919 | 938 | 957 | 976 | 995 | 1014 |
| 0.008 | 863 | 882 | 901 | 920 | 939 | 958 | 977 | 996 | 1015 |
| 0.009 | 864 | 883 | 902 | 921 | 940 | 959 | 978 | 997 | 1016 |
| 0.010 | 865 | 884 | 903 | 922 | 941 | 960 | 979 | 998 | 1017 |
| 0.020 | 866 | 885 | 904 | 923 | 942 | 961 | 980 | 999 | 1018 |
| 0.030 | 867 | 886 | 905 | 924 | 943 | 962 | 981 | 1000 | 1019 |
| 0.040 | 868 | 887 | 906 | 925 | 944 | 963 | 982 | 1001 | 1020 |
| 0.050 | 869 | 888 | 907 | 926 | 945 | 964 | 983 | 1002 | 1021 |
| 0.060 | 870 | 889 | 908 | 927 | 946 | 965 | 984 | 1003 | 1022 |
| 0.070 | 871 | 890 | 909 | 928 | 947 | 966 | 985 | 1004 | 1023 |

TABLE 3-continued

Effective Amounts of Bimatoprost and Levobunolol

| | | | | | | | | | |
|---|---|---|---|---|---|---|---|---|---|
| 0.080 | 872 | 891 | 910 | 929 | 948 | 967 | 986 | 1005 | 1024 |
| 0.090 | 873 | 892 | 911 | 930 | 949 | 968 | 987 | 1006 | 1025 |
| 0.100 | 874 | 893 | 912 | 931 | 950 | 969 | 988 | 1007 | 1026 |

TABLE 4

Effective Amounts of Bimatoprost and Metipranolol

| Bimatoprost | Metipranolol % w/w | | | | | | | | | | | | | |
|---|---|---|---|---|---|---|---|---|---|---|---|---|---|---|
| % w/w | 0.0030 | 0.0040 | 0.0060 | 0.0080 | 0.01 | 0.03 | 0.04 | 0.06 | 0.08 | 0.10 | 0.15 | 0.20 | 0.25 | 0.30 |
| 0.001 | 1027 | 1046 | 1065 | 1084 | 1103 | 1122 | 1141 | 1160 | 1179 | 1198 | 1217 | 1236 | 1255 | 1274 |
| 0.002 | 1028 | 1047 | 1066 | 1085 | 1104 | 1123 | 1142 | 1161 | 1180 | 1199 | 1218 | 1237 | 1256 | 1275 |
| 0.003 | 1029 | 1048 | 1067 | 1086 | 1105 | 1124 | 1143 | 1162 | 1181 | 1200 | 1219 | 1238 | 1257 | 1276 |
| 0.004 | 1030 | 1049 | 1068 | 1087 | 1106 | 1125 | 1144 | 1163 | 1182 | 1201 | 1220 | 1239 | 1258 | 1277 |
| 0.005 | 1031 | 1050 | 1069 | 1088 | 1107 | 1126 | 1145 | 1164 | 1183 | 1202 | 1221 | 1240 | 1259 | 1278 |
| 0.006 | 1032 | 1051 | 1070 | 1089 | 1108 | 1127 | 1146 | 1165 | 1184 | 1203 | 1222 | 1241 | 1260 | 1279 |
| 0.007 | 1033 | 1052 | 1071 | 1090 | 1109 | 1128 | 1147 | 1166 | 1185 | 1204 | 1223 | 1242 | 1261 | 1280 |
| 0.008 | 1034 | 1053 | 1072 | 1091 | 1110 | 1129 | 1148 | 1167 | 1186 | 1205 | 1224 | 1243 | 1262 | 1281 |
| 0.009 | 1035 | 1054 | 1073 | 1092 | 1111 | 1130 | 1149 | 1168 | 1187 | 1206 | 1225 | 1244 | 1263 | 1282 |
| 0.010 | 1036 | 1055 | 1074 | 1093 | 1112 | 1131 | 1150 | 1169 | 1188 | 1207 | 1226 | 1245 | 1264 | 1283 |
| 0.020 | 1037 | 1056 | 1075 | 1094 | 1113 | 1132 | 1151 | 1170 | 1189 | 1208 | 1227 | 1246 | 1265 | 1284 |
| 0.030 | 1038 | 1057 | 1076 | 1095 | 1114 | 1133 | 1152 | 1171 | 1190 | 1209 | 1228 | 1247 | 1266 | 1285 |
| 0.040 | 1039 | 1058 | 1077 | 1096 | 1115 | 1134 | 1153 | 1172 | 1191 | 1210 | 1229 | 1248 | 1267 | 1286 |
| 0.050 | 1040 | 1059 | 1078 | 1097 | 1116 | 1135 | 1154 | 1173 | 1192 | 1211 | 1230 | 1249 | 1268 | 1287 |
| 0.060 | 1041 | 1060 | 1079 | 1098 | 1117 | 1136 | 1155 | 1174 | 1193 | 1212 | 1231 | 1250 | 1269 | 1288 |
| 0.070 | 1042 | 1061 | 1080 | 1099 | 1118 | 1137 | 1156 | 1175 | 1194 | 1213 | 1232 | 1251 | 1270 | 1289 |
| 0.080 | 1043 | 1062 | 1081 | 1100 | 1119 | 1138 | 1157 | 1176 | 1195 | 1214 | 1233 | 1252 | 1271 | 1290 |
| 0.090 | 1044 | 1063 | 1082 | 1101 | 1120 | 1139 | 1158 | 1177 | 1196 | 1215 | 1234 | 1253 | 1272 | 1291 |
| 0.100 | 1045 | 1064 | 1083 | 1102 | 1121 | 1140 | 1159 | 1178 | 1197 | 1216 | 1235 | 1254 | 1273 | 1292 |

TABLE 5

Effective Amounts of Travoprost and Timolol

| Travoprost | Timolol % w/w | | | | | | | |
|---|---|---|---|---|---|---|---|---|
| % w/w | 0.0002 | 0.0004 | 0.0006 | 0.0008 | 0.0010 | 0.0020 | 0.0040 | 0.0060 | 0.0080 |
| 0.0002 | 1293 | 1308 | 1323 | 1338 | 1353 | 1368 | 1383 | 1398 | 1413 |
| 0.0004 | 1294 | 1309 | 1324 | 1339 | 1354 | 1369 | 1384 | 1399 | 1414 |
| 0.0006 | 1295 | 1310 | 1325 | 1340 | 1355 | 1370 | 1385 | 1400 | 1415 |
| 0.0008 | 1296 | 1311 | 1326 | 1341 | 1356 | 1371 | 1386 | 1401 | 1416 |
| 0.0010 | 1297 | 1312 | 1327 | 1342 | 1357 | 1372 | 1387 | 1402 | 1417 |
| 0.0020 | 1298 | 1313 | 1328 | 1343 | 1358 | 1373 | 1388 | 1403 | 1418 |
| 0.0040 | 1299 | 1314 | 1329 | 1344 | 1359 | 1374 | 1389 | 1404 | 1419 |
| 0.0060 | 1300 | 1315 | 1330 | 1345 | 1360 | 1375 | 1390 | 1405 | 1420 |
| 0.0080 | 1301 | 1316 | 1331 | 1346 | 1361 | 1376 | 1391 | 1406 | 1421 |
| 0.0100 | 1302 | 1317 | 1332 | 1347 | 1362 | 1377 | 1392 | 1407 | 1422 |
| 0.0200 | 1303 | 1318 | 1333 | 1348 | 1363 | 1378 | 1393 | 1408 | 1423 |
| 0.0400 | 1304 | 1319 | 1334 | 1349 | 1364 | 1379 | 1394 | 1409 | 1424 |
| 0.0600 | 1305 | 1320 | 1335 | 1350 | 1365 | 1380 | 1395 | 1410 | 1425 |
| 0.0800 | 1306 | 1321 | 1336 | 1351 | 1366 | 1381 | 1396 | 1411 | 1426 |
| 0.1000 | 1307 | 1322 | 1337 | 1352 | 1367 | 1382 | 1397 | 1412 | 1427 |

| Travoprost | Timolol % w/w | | | | | | | |
|---|---|---|---|---|---|---|---|---|
| % w/w | 0.01 | 0.02 | 0.04 | 0.06 | 0.08 | 0.10 | 0.15 | 0.20 | 0.25 |
| 0.0002 | 1428 | 1443 | 1458 | 1473 | 1488 | 1503 | 1518 | 1533 | 1548 |
| 0.0004 | 1429 | 1444 | 1459 | 1474 | 1489 | 1504 | 1519 | 1534 | 1549 |
| 0.0006 | 1430 | 1445 | 1460 | 1475 | 1490 | 1505 | 1520 | 1535 | 1550 |
| 0.0008 | 1431 | 1446 | 1461 | 1476 | 1491 | 1506 | 1521 | 1536 | 1551 |
| 0.0010 | 1432 | 1447 | 1462 | 1477 | 1492 | 1507 | 1522 | 1537 | 1552 |
| 0.0020 | 1433 | 1448 | 1463 | 1478 | 1493 | 1508 | 1523 | 1538 | 1553 |
| 0.0040 | 1434 | 1449 | 1464 | 1479 | 1494 | 1509 | 1524 | 1539 | 1554 |
| 0.0060 | 1435 | 1450 | 1465 | 1480 | 1495 | 1510 | 1525 | 1540 | 1555 |
| 0.0080 | 1436 | 1451 | 1466 | 1481 | 1496 | 1511 | 1526 | 1541 | 1556 |
| 0.0100 | 1437 | 1452 | 1467 | 1482 | 1497 | 1512 | 1527 | 1542 | 1557 |
| 0.0200 | 1438 | 1453 | 1468 | 1483 | 1498 | 1513 | 1528 | 1543 | 1558 |
| 0.0400 | 1439 | 1454 | 1469 | 1484 | 1499 | 1514 | 1529 | 1544 | 1559 |
| 0.0600 | 1440 | 1455 | 1470 | 1485 | 1500 | 1515 | 1530 | 1545 | 1560 |

TABLE 5-continued

Effective Amounts of Travoprost and Timolol

| | 0.0800 | 1441 | 1456 | 1471 | 1486 | 1501 | 1516 | 1531 | 1546 | 1561 |
|---|---|---|---|---|---|---|---|---|---|---|
| | 0.1000 | 1442 | 1457 | 1472 | 1487 | 1502 | 1517 | 1532 | 1547 | 1562 |

TABLE 6

Effective Amounts of Travoprost and Betaxolol

| Travoprost | Betaxolol % w/w | | | | | | | | |
|---|---|---|---|---|---|---|---|---|---|
| % w/w | 0.0002 | 0.0004 | 0.0006 | 0.0008 | 0.0010 | 0.0020 | 0.0040 | 0.0060 | 0.0080 |
| 0.0002 | 1563 | 1578 | 1593 | 1608 | 1623 | 1638 | 1653 | 1668 | 1683 |
| 0.0004 | 1564 | 1579 | 1594 | 1609 | 1624 | 1639 | 1654 | 1669 | 1684 |
| 0.0006 | 1565 | 1580 | 1595 | 1610 | 1625 | 1640 | 1655 | 1670 | 1685 |
| 0.0008 | 1566 | 1581 | 1596 | 1611 | 1626 | 1641 | 1656 | 1671 | 1686 |
| 0.0010 | 1567 | 1582 | 1597 | 1612 | 1627 | 1642 | 1657 | 1672 | 1687 |
| 0.0020 | 1568 | 1583 | 1598 | 1613 | 1628 | 1643 | 1658 | 1673 | 1688 |
| 0.0040 | 1569 | 1584 | 1599 | 1614 | 1629 | 1644 | 1659 | 1674 | 1689 |
| 0.0060 | 1570 | 1585 | 1600 | 1615 | 1630 | 1645 | 1660 | 1675 | 1690 |
| 0.0080 | 1571 | 1586 | 1601 | 1616 | 1631 | 1646 | 1661 | 1676 | 1691 |
| 0.0100 | 1572 | 1587 | 1602 | 1617 | 1632 | 1647 | 1662 | 1677 | 1692 |
| 0.0200 | 1573 | 1588 | 1603 | 1618 | 1633 | 1648 | 1663 | 1678 | 1693 |
| 0.0400 | 1574 | 1589 | 1604 | 1619 | 1634 | 1649 | 1664 | 1679 | 1694 |
| 0.0600 | 1575 | 1590 | 1605 | 1620 | 1635 | 1650 | 1665 | 1680 | 1695 |
| 0.0800 | 1576 | 1591 | 1606 | 1621 | 1636 | 1651 | 1666 | 1681 | 1696 |
| 0.1000 | 1577 | 1592 | 1607 | 1622 | 1637 | 1652 | 1667 | 1682 | 1697 |

| Travoprost | Betaxolol % w/w | | | | | | | | |
|---|---|---|---|---|---|---|---|---|---|
| % w/w | 0.01 | 0.02 | 0.04 | 0.06 | 0.08 | 0.10 | 0.15 | 0.20 | 0.25 |
| 0.0002 | 1698 | 1713 | 1728 | 1743 | 1758 | 1773 | 1788 | 1803 | 1818 |
| 0.0004 | 1699 | 1714 | 1729 | 1744 | 1759 | 1774 | 1789 | 1804 | 1819 |
| 0.0006 | 1700 | 1715 | 1730 | 1745 | 1760 | 1775 | 1790 | 1805 | 1820 |
| 0.0008 | 1701 | 1716 | 1731 | 1746 | 1761 | 1776 | 1791 | 1806 | 1821 |
| 0.0010 | 1702 | 1717 | 1732 | 1747 | 1762 | 1777 | 1792 | 1807 | 1822 |
| 0.0020 | 1703 | 1718 | 1733 | 1748 | 1763 | 1778 | 1793 | 1808 | 1823 |
| 0.0040 | 1704 | 1719 | 1734 | 1749 | 1764 | 1779 | 1794 | 1809 | 1824 |
| 0.0060 | 1705 | 1720 | 1735 | 1750 | 1765 | 1780 | 1795 | 1810 | 1825 |
| 0.0080 | 1706 | 1721 | 1736 | 1751 | 1766 | 1781 | 1796 | 1811 | 1826 |
| 0.0100 | 1707 | 1722 | 1737 | 1752 | 1767 | 1782 | 1797 | 1812 | 1827 |
| 0.0200 | 1708 | 1723 | 1738 | 1753 | 1768 | 1783 | 1798 | 1813 | 1828 |
| 0.0400 | 1709 | 1724 | 1739 | 1754 | 1769 | 1784 | 1799 | 1814 | 1829 |
| 0.0600 | 1710 | 1725 | 1740 | 1755 | 1770 | 1785 | 1800 | 1815 | 1830 |
| 0.0800 | 1711 | 1726 | 1741 | 1756 | 1771 | 1786 | 1801 | 1816 | 1831 |
| 0.1000 | 1712 | 1727 | 1742 | 1757 | 1772 | 1787 | 1802 | 1817 | 1832 |

TABLE 7

Effective Amounts of Travoprost and Levobunolol

| Travoprost | Levobunolol % w/w | | | | | | | | |
|---|---|---|---|---|---|---|---|---|---|
| % w/w | 0.0002 | 0.0004 | 0.0006 | 0.0008 | 0.0010 | 0.0020 | 0.0040 | 0.0060 | 0.0080 |
| 0.0002 | 1833 | 1848 | 1863 | 1878 | 1893 | 1908 | 1923 | 1938 | 1953 |
| 0.0004 | 1834 | 1849 | 1864 | 1879 | 1894 | 1909 | 1924 | 1939 | 1954 |
| 0.0006 | 1835 | 1850 | 1865 | 1880 | 1895 | 1910 | 1925 | 1940 | 1955 |
| 0.0008 | 1836 | 1851 | 1866 | 1881 | 1896 | 1911 | 1926 | 1941 | 1956 |
| 0.0010 | 1837 | 1852 | 1867 | 1882 | 1897 | 1912 | 1927 | 1942 | 1957 |
| 0.0020 | 1838 | 1853 | 1868 | 1883 | 1898 | 1913 | 1928 | 1943 | 1958 |
| 0.0040 | 1839 | 1854 | 1869 | 1884 | 1899 | 1914 | 1929 | 1944 | 1959 |
| 0.0060 | 1840 | 1855 | 1870 | 1885 | 1900 | 1915 | 1930 | 1945 | 1960 |
| 0.0080 | 1841 | 1856 | 1871 | 1886 | 1901 | 1916 | 1931 | 1946 | 1961 |
| 0.0100 | 1842 | 1857 | 1872 | 1887 | 1902 | 1917 | 1932 | 1947 | 1962 |
| 0.0200 | 1843 | 1858 | 1873 | 1888 | 1903 | 1918 | 1933 | 1948 | 1963 |
| 0.0400 | 1844 | 1859 | 1874 | 1889 | 1904 | 1919 | 1934 | 1949 | 1964 |
| 0.0600 | 1845 | 1860 | 1875 | 1890 | 1905 | 1920 | 1935 | 1950 | 1965 |
| 0.0800 | 1846 | 1861 | 1876 | 1891 | 1906 | 1921 | 1936 | 1951 | 1966 |
| 0.1000 | 1847 | 1862 | 1877 | 1892 | 1907 | 1922 | 1937 | 1952 | 1967 |

TABLE 7-continued

Effective Amounts of Travoprost and Levobunolol

| Travoprost | Levobunolol % w/w | | | | | | | | |
|---|---|---|---|---|---|---|---|---|---|
| % w/w | 0.01 | 0.02 | 0.04 | 0.06 | 0.08 | 0.10 | 0.15 | 0.20 | 0.25 |
| 0.0002 | 1968 | 1983 | 1998 | 2013 | 2028 | 2043 | 2058 | 2073 | 2088 |
| 0.0004 | 1969 | 1984 | 1999 | 2014 | 2029 | 2044 | 2059 | 2074 | 2089 |
| 0.0006 | 1970 | 1985 | 2000 | 2015 | 2030 | 2045 | 2060 | 2075 | 2090 |
| 0.0008 | 1971 | 1986 | 2001 | 2016 | 2031 | 2046 | 2061 | 2076 | 2091 |
| 0.0010 | 1972 | 1987 | 2002 | 2017 | 2032 | 2047 | 2062 | 2077 | 2092 |
| 0.0020 | 1973 | 1988 | 2003 | 2018 | 2033 | 2048 | 2063 | 2078 | 2093 |
| 0.0040 | 1974 | 1989 | 2004 | 2019 | 2034 | 2049 | 2064 | 2079 | 2094 |
| 0.0060 | 1975 | 1990 | 2005 | 2020 | 2035 | 2050 | 2065 | 2080 | 2095 |
| 0.0080 | 1976 | 1991 | 2006 | 2021 | 2036 | 2051 | 2066 | 2081 | 2096 |
| 0.0100 | 1977 | 1992 | 2007 | 2022 | 2037 | 2052 | 2067 | 2082 | 2097 |
| 0.0200 | 1978 | 1993 | 2008 | 2023 | 2038 | 2053 | 2068 | 2083 | 2098 |
| 0.0400 | 1979 | 1994 | 2009 | 2024 | 2039 | 2054 | 2069 | 2084 | 2099 |
| 0.0600 | 1980 | 1995 | 2010 | 2025 | 2040 | 2055 | 2070 | 2085 | 2100 |
| 0.0800 | 1981 | 1996 | 2011 | 2026 | 2041 | 2056 | 2071 | 2086 | 2101 |
| 0.1000 | 1982 | 1997 | 2012 | 2027 | 2042 | 2057 | 2072 | 2087 | 2102 |

TABLE 8

Effective Amounts of Travoprost and Metipranolol

| Travoprost % w/w | Metipranolol % w/w | | | | | | | | | | | | | |
|---|---|---|---|---|---|---|---|---|---|---|---|---|---|---|
| | 0.0030 | 0.0040 | 0.0060 | 0.0080 | 0.01 | 0.03 | 0.04 | 0.06 | 0.08 | 0.10 | 0.15 | 0.20 | 0.25 | 0.30 |
| 0.0002 | 2103 | 2118 | 2133 | 2148 | 2163 | 2178 | 2193 | 2208 | 2223 | 2238 | 2253 | 2268 | 2283 | 2298 |
| 0.0004 | 2104 | 2119 | 2134 | 2149 | 2164 | 2179 | 2194 | 2209 | 2224 | 2239 | 2254 | 2269 | 2284 | 2299 |
| 0.0006 | 2105 | 2120 | 2135 | 2150 | 2165 | 2180 | 2195 | 2210 | 2225 | 2240 | 2255 | 2270 | 2285 | 2300 |
| 0.0008 | 2106 | 2121 | 2136 | 2151 | 2166 | 2181 | 2196 | 2211 | 2226 | 2241 | 2256 | 2271 | 2286 | 2301 |
| 0.0010 | 2107 | 2122 | 2137 | 2152 | 2167 | 2182 | 2197 | 2212 | 2227 | 2242 | 2257 | 2272 | 2287 | 2302 |
| 0.0020 | 2108 | 2123 | 2138 | 2153 | 2168 | 2183 | 2198 | 2213 | 2228 | 2243 | 2258 | 2273 | 2288 | 2303 |
| 0.0040 | 2109 | 2124 | 2139 | 2154 | 2169 | 2184 | 2199 | 2214 | 2229 | 2244 | 2259 | 2274 | 2289 | 2304 |
| 0.0060 | 2110 | 2125 | 2140 | 2155 | 2170 | 2185 | 2200 | 2215 | 2230 | 2245 | 2260 | 2275 | 2290 | 2305 |
| 0.0080 | 2111 | 2126 | 2141 | 2156 | 2171 | 2186 | 2201 | 2216 | 2231 | 2246 | 2261 | 2276 | 2291 | 2306 |
| 0.0100 | 2112 | 2127 | 2142 | 2157 | 2172 | 2187 | 2202 | 2217 | 2232 | 2247 | 2262 | 2277 | 2292 | 2307 |
| 0.0200 | 2113 | 2128 | 2143 | 2158 | 2173 | 2188 | 2203 | 2218 | 2233 | 2248 | 2263 | 2278 | 2293 | 2308 |
| 0.0400 | 2114 | 2129 | 2144 | 2159 | 2174 | 2189 | 2204 | 2219 | 2234 | 2249 | 2264 | 2279 | 2294 | 2309 |
| 0.0600 | 2115 | 2130 | 2145 | 2160 | 2175 | 2190 | 2205 | 2220 | 2235 | 2250 | 2265 | 2280 | 2295 | 2310 |
| 0.0800 | 2116 | 2131 | 2146 | 2161 | 2176 | 2191 | 2206 | 2221 | 2236 | 2251 | 2266 | 2281 | 2296 | 2311 |
| 0.1000 | 2117 | 2132 | 2147 | 2162 | 2177 | 2192 | 2207 | 2222 | 2237 | 2252 | 2267 | 2282 | 2297 | 2312 |

TABLE 9

Effective Amounts of Latanoprost and Timolol

| Latanoprost | Timolol % w/w | | | | | | | | |
|---|---|---|---|---|---|---|---|---|---|
| % w/w | 0.0002 | 0.0004 | 0.0006 | 0.0008 | 0.0010 | 0.0020 | 0.0040 | 0.0060 | 0.0080 |
| 0.0003 | 2313 | 2328 | 2343 | 2358 | 2373 | 2388 | 2403 | 2418 | 2433 |
| 0.0005 | 2314 | 2329 | 2344 | 2359 | 2374 | 2389 | 2404 | 2419 | 2434 |
| 0.0007 | 2315 | 2330 | 2345 | 2360 | 2375 | 2390 | 2405 | 2420 | 2435 |
| 0.0009 | 2316 | 2331 | 2346 | 2361 | 2376 | 2391 | 2406 | 2421 | 2436 |
| 0.0010 | 2317 | 2332 | 2347 | 2362 | 2377 | 2392 | 2407 | 2422 | 2437 |
| 0.0030 | 2318 | 2333 | 2348 | 2363 | 2378 | 2393 | 2408 | 2423 | 2438 |
| 0.0050 | 2319 | 2334 | 2349 | 2364 | 2379 | 2394 | 2409 | 2424 | 2439 |
| 0.0070 | 2320 | 2335 | 2350 | 2365 | 2380 | 2395 | 2410 | 2425 | 2440 |
| 0.0090 | 2321 | 2336 | 2351 | 2366 | 2381 | 2396 | 2411 | 2426 | 2441 |
| 0.0100 | 2322 | 2337 | 2352 | 2367 | 2382 | 2397 | 2412 | 2427 | 2442 |
| 0.0300 | 2323 | 2338 | 2353 | 2368 | 2383 | 2398 | 2413 | 2428 | 2443 |
| 0.0500 | 2324 | 2339 | 2354 | 2369 | 2384 | 2399 | 2414 | 2429 | 2444 |
| 0.0700 | 2325 | 2340 | 2355 | 2370 | 2385 | 2400 | 2415 | 2430 | 2445 |
| 0.0900 | 2326 | 2341 | 2356 | 2371 | 2386 | 2401 | 2416 | 2431 | 2446 |
| 0.1000 | 2327 | 2342 | 2357 | 2372 | 2387 | 2402 | 2417 | 2432 | 2447 |

TABLE 9-continued

Effective Amounts of Latanoprost and Timolol

| Latanoprost | Timolol % w/w | | | | | | | | |
|---|---|---|---|---|---|---|---|---|---|
| % w/w | 0.01 | 0.02 | 0.04 | 0.06 | 0.08 | 0.10 | 0.15 | 0.20 | 0.25 |
| 0.0003 | 2448 | 2463 | 2478 | 2493 | 2508 | 2523 | 2538 | 2553 | 2568 |
| 0.0005 | 2449 | 2464 | 2479 | 2494 | 2509 | 2524 | 2539 | 2554 | 2569 |
| 0.0007 | 2450 | 2465 | 2480 | 2495 | 2510 | 2525 | 2540 | 2555 | 2570 |
| 0.0009 | 2451 | 2466 | 2481 | 2496 | 2511 | 2526 | 2541 | 2556 | 2571 |
| 0.0010 | 2452 | 2467 | 2482 | 2497 | 2512 | 2527 | 2542 | 2557 | 2572 |
| 0.0030 | 2453 | 2468 | 2483 | 2498 | 2513 | 2528 | 2543 | 2558 | 2573 |
| 0.0050 | 2454 | 2469 | 2484 | 2499 | 2514 | 2529 | 2544 | 2559 | 2574 |
| 0.0070 | 2455 | 2470 | 2485 | 2500 | 2515 | 2530 | 2545 | 2560 | 2575 |
| 0.0090 | 2456 | 2471 | 2486 | 2501 | 2516 | 2531 | 2546 | 2561 | 2576 |
| 0.0100 | 2457 | 2472 | 2487 | 2502 | 2517 | 2532 | 2547 | 2562 | 2577 |
| 0.0300 | 2458 | 2473 | 2488 | 2503 | 2518 | 2533 | 2548 | 2563 | 2578 |
| 0.0500 | 2459 | 2474 | 2489 | 2504 | 2519 | 2534 | 2549 | 2564 | 2579 |
| 0.0700 | 2460 | 2475 | 2490 | 2505 | 2520 | 2535 | 2550 | 2565 | 2580 |
| 0.0900 | 2461 | 2476 | 2491 | 2506 | 2521 | 2536 | 2551 | 2566 | 2581 |
| 0.1000 | 2462 | 2477 | 2492 | 2507 | 2522 | 2537 | 2552 | 2567 | 2582 |

TABLE 10

Effective Amounts of Latanoprost and Betaxolol

| Latanoprost | Betaxolol % w/w | | | | | | | | |
|---|---|---|---|---|---|---|---|---|---|
| % w/w | 0.0002 | 0.0004 | 0.0006 | 0.0008 | 0.0010 | 0.0020 | 0.0040 | 0.0060 | 0.0080 |
| 0.0003 | 2583 | 2598 | 2613 | 2628 | 2643 | 2658 | 2673 | 2688 | 2703 |
| 0.0005 | 2584 | 2599 | 2614 | 2629 | 2644 | 2659 | 2674 | 2689 | 2704 |
| 0.0007 | 2585 | 2600 | 2615 | 2630 | 2645 | 2660 | 2675 | 2690 | 2705 |
| 0.0009 | 2586 | 2601 | 2616 | 2631 | 2646 | 2661 | 2676 | 2691 | 2706 |
| 0.0010 | 2587 | 2602 | 2617 | 2632 | 2647 | 2662 | 2677 | 2692 | 2707 |
| 0.0030 | 2588 | 2603 | 2618 | 2633 | 2648 | 2663 | 2678 | 2693 | 2708 |
| 0.0050 | 2589 | 2604 | 2619 | 2634 | 2649 | 2664 | 2679 | 2694 | 2709 |
| 0.0070 | 2590 | 2605 | 2620 | 2635 | 2650 | 2665 | 2680 | 2695 | 2710 |
| 0.0090 | 2591 | 2606 | 2621 | 2636 | 2651 | 2666 | 2681 | 2696 | 2711 |
| 0.0100 | 2592 | 2607 | 2622 | 2637 | 2652 | 2667 | 2682 | 2697 | 2712 |
| 0.0300 | 2593 | 2608 | 2623 | 2638 | 2653 | 2668 | 2683 | 2698 | 2713 |
| 0.0500 | 2594 | 2609 | 2624 | 2639 | 2654 | 2669 | 2684 | 2699 | 2714 |
| 0.0700 | 2595 | 2610 | 2625 | 2640 | 2655 | 2670 | 2685 | 2700 | 2715 |
| 0.0900 | 2596 | 2611 | 2626 | 2641 | 2656 | 2671 | 2686 | 2701 | 2716 |
| 0.1000 | 2597 | 2612 | 2627 | 2642 | 2657 | 2672 | 2687 | 2702 | 2717 |

| Latanoprost | Betaxolol % w/w | | | | | | | | |
|---|---|---|---|---|---|---|---|---|---|
| % w/w | 0.01 | 0.02 | 0.04 | 0.06 | 0.08 | 0.10 | 0.15 | 0.20 | 0.25 |
| 0.0003 | 2718 | 2733 | 2748 | 2763 | 2778 | 2793 | 2808 | 2823 | 2838 |
| 0.0005 | 2719 | 2734 | 2749 | 2764 | 2779 | 2794 | 2809 | 2824 | 2839 |
| 0.0007 | 2720 | 2735 | 2750 | 2765 | 2780 | 2795 | 2810 | 2825 | 2840 |
| 0.0009 | 2721 | 2736 | 2751 | 2766 | 2781 | 2796 | 2811 | 2826 | 2841 |
| 0.0010 | 2722 | 2737 | 2752 | 2767 | 2782 | 2797 | 2812 | 2827 | 2842 |
| 0.0030 | 2723 | 2738 | 2753 | 2768 | 2783 | 2798 | 2813 | 2828 | 2843 |
| 0.0050 | 2724 | 2739 | 2754 | 2769 | 2784 | 2799 | 2814 | 2829 | 2844 |
| 0.0070 | 2725 | 2740 | 2755 | 2770 | 2785 | 2800 | 2815 | 2830 | 2845 |
| 0.0090 | 2726 | 2741 | 2756 | 2771 | 2786 | 2801 | 2816 | 2831 | 2846 |
| 0.0100 | 2727 | 2742 | 2757 | 2772 | 2787 | 2802 | 2817 | 2832 | 2847 |
| 0.0300 | 2728 | 2743 | 2758 | 2773 | 2788 | 2803 | 2818 | 2833 | 2848 |
| 0.0500 | 2729 | 2744 | 2759 | 2774 | 2789 | 2804 | 2819 | 2834 | 2849 |
| 0.0700 | 2730 | 2745 | 2760 | 2775 | 2790 | 2805 | 2820 | 2835 | 2850 |
| 0.0900 | 2731 | 2746 | 2761 | 2776 | 2791 | 2806 | 2821 | 2836 | 2851 |
| 0.1000 | 2732 | 2747 | 2762 | 2777 | 2792 | 2807 | 2822 | 2837 | 2852 |

TABLE 11

Effective Amounts of Latanoprost and Levobunolol

| Latanoprost % w/w | Levobunolol % w/w | | | | | | | | |
|---|---|---|---|---|---|---|---|---|---|
| | 0.0002 | 0.0004 | 0.0006 | 0.0008 | 0.0010 | 0.0020 | 0.0040 | 0.0060 | 0.0080 |
| 0.0003 | 2853 | 2868 | 2883 | 2898 | 2913 | 2928 | 2943 | 2958 | 2973 |
| 0.0005 | 2854 | 2869 | 2884 | 2899 | 2914 | 2929 | 2944 | 2959 | 2974 |
| 0.0007 | 2855 | 2870 | 2885 | 2900 | 2915 | 2930 | 2945 | 2960 | 2975 |
| 0.0009 | 2856 | 2871 | 2886 | 2901 | 2916 | 2931 | 2946 | 2961 | 2976 |
| 0.0010 | 2857 | 2872 | 2887 | 2902 | 2917 | 2932 | 2947 | 2962 | 2977 |
| 0.0030 | 2858 | 2873 | 2888 | 2903 | 2918 | 2933 | 2948 | 2963 | 2978 |
| 0.0050 | 2859 | 2874 | 2889 | 2904 | 2919 | 2934 | 2949 | 2964 | 2979 |
| 0.0070 | 2860 | 2875 | 2890 | 2905 | 2920 | 2935 | 2950 | 2965 | 2980 |
| 0.0090 | 2861 | 2876 | 2891 | 2906 | 2921 | 2936 | 2951 | 2966 | 2981 |
| 0.0100 | 2862 | 2877 | 2892 | 2907 | 2922 | 2937 | 2952 | 2967 | 2982 |
| 0.0300 | 2863 | 2878 | 2893 | 2908 | 2923 | 2938 | 2953 | 2968 | 2983 |
| 0.0500 | 2864 | 2879 | 2894 | 2909 | 2924 | 2939 | 2954 | 2969 | 2984 |
| 0.0700 | 2865 | 2880 | 2895 | 2910 | 2925 | 2940 | 2955 | 2970 | 2985 |
| 0.0900 | 2866 | 2881 | 2896 | 2911 | 2926 | 2941 | 2956 | 2971 | 2986 |
| 0.1000 | 2867 | 2882 | 2897 | 2912 | 2927 | 2942 | 2957 | 2972 | 2987 |

| Latanoprost % w/w | Levobunolol % w/w | | | | | | | | |
|---|---|---|---|---|---|---|---|---|---|
| | 0.01 | 0.02 | 0.04 | 0.06 | 0.08 | 0.10 | 0.15 | 0.20 | 0.25 |
| 0.0003 | 2988 | 3003 | 3018 | 3033 | 3048 | 3063 | 3078 | 3093 | 3108 |
| 0.0005 | 2989 | 3004 | 3019 | 3034 | 3049 | 3064 | 3079 | 3094 | 3109 |
| 0.0007 | 2990 | 3005 | 3020 | 3035 | 3050 | 3065 | 3080 | 3095 | 3110 |
| 0.0009 | 2991 | 3006 | 3021 | 3036 | 3051 | 3066 | 3081 | 3096 | 3111 |
| 0.0010 | 2992 | 3007 | 3022 | 3037 | 3052 | 3067 | 3082 | 3097 | 3112 |
| 0.0030 | 2993 | 3008 | 3023 | 3038 | 3053 | 3068 | 3083 | 3098 | 3113 |
| 0.0050 | 2994 | 3009 | 3024 | 3039 | 3054 | 3069 | 3084 | 3099 | 3114 |
| 0.0070 | 2995 | 3010 | 3025 | 3040 | 3055 | 3070 | 3085 | 3100 | 3115 |
| 0.0090 | 2996 | 3011 | 3026 | 3041 | 3056 | 3071 | 3086 | 3101 | 3116 |
| 0.0100 | 2997 | 3012 | 3027 | 3042 | 3057 | 3072 | 3087 | 3102 | 3117 |
| 0.0300 | 2998 | 3013 | 3028 | 3043 | 3058 | 3073 | 3088 | 3103 | 3118 |
| 0.0500 | 2999 | 3014 | 3029 | 3044 | 3059 | 3074 | 3089 | 3104 | 3119 |
| 0.0700 | 3000 | 3015 | 3030 | 3045 | 3060 | 3075 | 3090 | 3105 | 3120 |
| 0.0900 | 3001 | 3016 | 3031 | 3046 | 3061 | 3076 | 3091 | 3106 | 3121 |
| 0.1000 | 3002 | 3017 | 3032 | 3047 | 3062 | 3077 | 3092 | 3107 | 3122 |

TABLE 12

Effective Amounts of Latanoprost and Metipranolol

| Latanoprost % w/w | Metipranolol % w/w | | | | | | | | | | | | | |
|---|---|---|---|---|---|---|---|---|---|---|---|---|---|---|
| | 0.0030 | 0.0040 | 0.0060 | 0.0080 | 0.01 | 0.03 | 0.04 | 0.06 | 0.08 | 0.10 | 0.15 | 0.20 | 0.25 | 0.30 |
| 0.0003 | 3123 | 3138 | 3153 | 3168 | 3183 | 3198 | 3213 | 3228 | 3243 | 3258 | 3273 | 3288 | 3303 | 3318 |
| 0.0005 | 3124 | 3139 | 3154 | 3169 | 3184 | 3199 | 3214 | 3229 | 3244 | 3259 | 3274 | 3289 | 3304 | 3319 |
| 0.0007 | 3125 | 3140 | 3155 | 3170 | 3185 | 3200 | 3215 | 3230 | 3245 | 3260 | 3275 | 3290 | 3305 | 3320 |
| 0.0009 | 3126 | 3141 | 3156 | 3171 | 3186 | 3201 | 3216 | 3231 | 3246 | 3261 | 3276 | 3291 | 3306 | 3321 |
| 0.0010 | 3127 | 3142 | 3157 | 3172 | 3187 | 3202 | 3217 | 3232 | 3247 | 3262 | 3277 | 3292 | 3307 | 3322 |
| 0.0030 | 3128 | 3143 | 3158 | 3173 | 3188 | 3203 | 3218 | 3233 | 3248 | 3263 | 3278 | 3293 | 3308 | 3323 |
| 0.0050 | 3129 | 3144 | 3159 | 3174 | 3189 | 3204 | 3219 | 3234 | 3249 | 3264 | 3279 | 3294 | 3309 | 3324 |
| 0.0070 | 3130 | 3145 | 3160 | 3175 | 3190 | 3205 | 3220 | 3235 | 3250 | 3265 | 3280 | 3295 | 3310 | 3325 |
| 0.0090 | 3131 | 3146 | 3161 | 3176 | 3191 | 3206 | 3221 | 3236 | 3251 | 3266 | 3281 | 3296 | 3311 | 3326 |
| 0.0100 | 3132 | 3147 | 3162 | 3177 | 3192 | 3207 | 3222 | 3237 | 3252 | 3267 | 3282 | 3297 | 3312 | 3327 |
| 0.0300 | 3133 | 3148 | 3163 | 3178 | 3193 | 3208 | 3223 | 3238 | 3253 | 3268 | 3283 | 3298 | 3313 | 3328 |
| 0.0500 | 3134 | 3149 | 3164 | 3179 | 3194 | 3209 | 3224 | 3239 | 3254 | 3269 | 3284 | 3299 | 3314 | 3329 |
| 0.0700 | 3135 | 3150 | 3165 | 3180 | 3195 | 3210 | 3225 | 3240 | 3255 | 3270 | 3285 | 3300 | 3315 | 3330 |
| 0.0900 | 3136 | 3151 | 3166 | 3181 | 3196 | 3211 | 3226 | 3241 | 3256 | 3271 | 3286 | 3301 | 3316 | 3331 |
| 0.1000 | 3137 | 3152 | 3167 | 3182 | 3197 | 3212 | 3227 | 3242 | 3257 | 3272 | 3287 | 3302 | 3317 | 3332 |

II. Methods of Treatment

Methods of treating an ophthalmic disease are provided, including methods of treating glaucoma. In particular, the methods according to the embodiments of the present invention are useful in decreasing IOP without causing conjunctival hyperemia. Some embodiments of the methods provided herein include applying an ophthalmic formulation described herein to the region on or around the eye, which can treat ophthalmic diseases by sustained administration of an effective amount of an active pharmaceutical ingredient (e.g., a prostaglandin agent) and a sub-therapeutic amount of an active pharmaceutical ingredient (e.g., a vasoconstrictor agent), as described herein, to the ophthalmic tissue (i.e. conjunctiva, lacrimal tissue or cornea). The methods provided herein further include administering any appropriate ophthalmically acceptable excipient.

In another aspect, a method of reducing increased intraocular pressure (IOP) in a subject in need thereof is provided. The method includes administering to the subject a therapeutically effective amount of an ophthalmic pharmaceutical formulation including a prostaglandin agent and a vasoconstrictor agent as provided herein. In some embodiments, the subject is in need of treatment for glaucoma. In other embodiments, the subject displays conjunctival hyperemia.

In some embodiments, the prostaglandin agent is present in a therapeutically effective amount and the vasoconstrictor agent is present in a sub-therapeutic amount. In other embodiments, the prostaglandin agent is bimatoprost and the vasoconstrictor agent is timolol. In some embodiments, the ophthalmic pharmaceutical formulation further includes a buffering agent, a tonicity agent, a salt, a thickening agent and a preservative. In other embodiments, the ophthalmic pharmaceutical formulation consists essentially of bimatoprost, timolol, a buffering agent, a tonicity agent, a salt, a thickening agent and a preservative. In some embodiments, the bimatoprost is present in a therapeutically effective amount and the timolol is present in a sub-therapeutic amount.

III. Examples

Embodiments of the present invention are further illustrated by the following examples, which are not to be construed in any way as imposing limitations upon the scope thereof. On the contrary, it is to be clearly understood that resort may be made to various other embodiments, modifications and equivalents, which, after reading the description provided herein, may suggest themselves to those skilled in the art without departing from the spirit of the invention.

Bimatoprost 0.03% (Lumigan®), given once daily, is a highly efficacious intraocular pressure (IOP) lowering drug (Chen J et al., *Optometry Pract* 2002; 3:95-102; Cohen J S et al., *Surv Ophthalmol* 2004; 49:S45-S52; Christiansen G A et al., *Ophthalmology* 2004; 111:1658-1662; DuBiner H et al., *Surv Ophthalmol* 2001; 45(Suppl 4):S353-S360; Eisenberg D L, Toris C B, Camras C B, *Surv Ophthalmol* 2002; 47:S105-S115; Gandolfi S A, Cimino L., *Ophthalmology* 2003; 110:609-614; Higginbotham E J, Schuman J S, Goldberg I, et al., *Arch Ophthalmol* 2002; 120:1286-1293; Noecker R S et al., *Am J Ophthalmol* 2003; 135:55-63; Parrish R K, Palmberg P, Sheu W-P., *Am J Ophthalmol* 2003; 135:688-703; Williams R D., *Adv Ther* 2002; 19:275-281). It has a very high systemic safety margin in studies conducted in laboratory animals (Woodward D F, Phelps R L, Krauss A H-P, et al., *Cardiovasc Drug Rev* 2004; 22:103-120). The most common ocular side effect associated with bimatoprost in humans is conjunctival hyperemia. This effect is usually mild and diminishes over time (Abelson M B et al., *Adv Ther* 2003; 20:1-13; Cohen J S et al., *Surv Ophthalmol* 2004; 49:S45-S52; DuBiner H et al., *Surv Ophthalmol* 2001; 45(Suppl 4):S353-S360; Eisenberg D L, Toris C B, Camras C B, *Surv Ophthalmol* 2002; 47:S105-S115; Higginbotham E J, Schuman J S, Goldberg I, et al., *Arch Ophthalmol* 2002; 120:1286-1293; Noecker R S et al., *Am J Ophthalmol* 2003; 135:55-63; Parrish R K, Palmberg P, Sheu W-P., *Am J Ophthalmol* 2003; 135:688-703; Stewart W C et al., *Am J Ophthalmol* 2003; 135:314-320).

Latanoprost (Xalatan®), a prostaglandin FP receptor agonist prodrug, is a well-established IOP lowering medication that has been used as a comparator for ocular hypotensive and conjunctival hyperemia effects (DuBiner H et al., *Surv Ophthalmol* 2001; 45(Suppl 4):5353-S360; Eisenberg D L, Toris C B, Camras C B, *Surv Ophthalmol* 2002; 47:S105-S115; Gandolfi S A, Cimino L., *Ophthalmology* 2003; 110:609-614; Noecker R S et al., *Am J Ophthalmol* 2003; 135:55-63; Parrish R K, Palmberg P, Sheu W-P., *Am J Ophthalmol* 2003; 135:688-703; Stewart W C et al., *Am J Ophthalmol* 2003; 135:314-320). Bimatoprost and latanoprost exhibit different pharmacological profiles and stimulate different receptor populations, bimatoprost-sensitive and prostanoid FP receptors, respectively (Chen J et al., *Br J Pharmacol* 2005; 144:493-501; Spada C S, Krauss A H-P, Woodward D F, et al., *Exp Eye Res* 2005; 80:135-145; Woodward D F, Krauss A H-P, Chen J, et al., *Surv. Ophthalmol* 2001; 45:S337-S345; Woodward D F, Krauss A H-P, Chen J, et al., *J Pharmacol Exp Ther* 2003; 305:772-785). Nevertheless, bimatoprost and prostanoid FP agonists have similarities with respect to endothelium-dependent vasodilatation in blood vessels (Astin M, Stjernschantz J, Selén G., *Exp Eye Res* 1994; 59:401-408; Astin M, Stjernschantz J., *Eur J Pharmacol* 1997; 340:195-201; Astin M, Stjernschantz J., *Curr Eye Res* 1997; 16:886-890; Astin M., *J Ocul Pharmacol* 1998; 14:119-128; Chen J. et al., *Br J Pharmacol* 1995; 116:3035-3041; Chen J, Woodward D F. *Adv Exp Med Biol* 2002; 507:331-336; Chen J et al., *Br J Pharmacol* 2005; 144:493-501; Stewart W C et al., *Am J Ophthalmol* 2003; 135:314-320) and stimulation of intracellular calcium signaling, but in different cell populations of the cat iris sphincter (Spada C S, Krauss A H-P, Woodward D F, et al., *Exp Eye Res* 2005; 80:135-145).

Vasorelaxation produced by the stimulation of endothelial muscarinic receptors and mediated by an endothelium-derived substance was originally discovered by Furchgott and Zawadzki (Furchgott R F, Zawadzki J V., *Nature* 1980; 288:373-376). This substance was identified as nitric oxide (NO) by numerous studies in the mid-1980s. In endothelial cells, increases in intracellular calcium activate endothelial nitric oxide synthase (eNOS) and lead to the generation of nitric oxide, an important regulator of ocular blood flow (Albrecht E W et al., *J Pathol* 2003; 1999:8-17; Koss M C., *Eur J Pharmacol* 1999; 374:161-174; Schmetterer L, Polak K, *Prog Retin Eye Res.* 2001; 20:823-847). All isoforms of NOS have been identified in eyes, including ocular surface cells (Kim J C et al., *J Korean Med Sci* 2002; 17:389-394; Schmetterer L, Polak K, *Prog Retin Eye Res.* 2001; 20:823-847). The endothelial NOS isoform, also referred to as NOS-3, has often been reported to have a protective role in a number of disease states and inflammatory processes (Albrecht E W et al., *J Pathol* 2003; 1999:8-17), but under certain conditions eNOS may also contribute to inflammatory responses (Cirino G, Fiorucci S, Sessa W C., *Trends Pharmacol Sci* 2003; 24:91-95).

Studies in patients have addressed the long-term safety of bimatoprost and the time course of bimatoprost-induced conjunctival hyperemia (Abelson M B et al., *Adv Ther* 2003; 20:1-13; Cohen J S et al., *Surv Ophthalmol* 2004; 49:S45-S52; Higginbotham E J, Schuman J S, Goldberg I, et al., *Arch Ophthalmol* 2002; 120:1286-1293). More recent studies investigated the inflammatory potential of bimatoprost using human conjunctival biopsies and cells (Guenoun J-M et al., *Invest Ophthalmol Vis Sci* 2005; 46:2444-2450; Leal B C et al., *Am J Ophthalmol* 2004; 138:310-313; Mroz M, Abelson M B et al., *Invest Ophthalmol Vis Sci* 2003; 44:ARVOE-Abstract 4417). However, information from humans is limited, so animal models have been used to investigate safety issues, the pharmacological mechanism of hyperemia, and the possible involvement of ocular surface inflammation. The ocular surface safety of topical bimatoprost treatment in animals was established in multiple-dose studies performed for the development of bimatoprost (Lumigan (Bimatoprost) Ophthalmic Solution. Pharmacology Review of New Drug Application 21-275. FDA/Center for Drug Evaluation and Research. 2001; Part 1 and Part 2:1-107. Available online at http://www.fda.gov/cder/foi/nda/2001/21275_Lumigan.htm). Other preclinical studies showed that hyperemic effects of bimatoprost on the vasculature occur by a non-inflammatory, nitric oxide-mediated vasodilatation.

Clinical Hyperemia

A month-long, multicenter, open-label study evaluated the onset and progression of conjunctival hyperemia associated with bimatoprost 0.03% once daily during 6 office visits (Abelson M B et al., Adv Ther 2003; 20:1-13). The 39 patients enrolled in the study had bilateral open-angle glaucoma or ocular hypertension and had not been treated previously with bimatoprost. An overall mean hyperemia score was calculated for each visit by averaging three vessel-bed scores obtained by slit-lamp biomicroscopy. The frequency and severity of hyperemia peaked approximately 1 day after the first instillation of bimatoprost and decreased consistently throughout the study, returning to near baseline levels by day 28 (Abelson M B et al., Adv Ther 2003; 20:1-13; FIG. 1). The hyperemia was considered not clinically significant.

The long-term safety of bimatoprost was compared to that of timolol in patients with glaucoma or ocular hypertension (Higginbotham E J, Schuman J S, Goldberg I, et al., Arch Ophthalmol 2002; 120:1286-1293). In two identical, multicenter, randomized, double-blind, 1-year clinical trials, patients were treated with bimatoprost 0.03% once daily (n=474), bimatoprost 0.03% twice daily (n=483), or timolol maleate 0.5% twice daily (n=241). Laser-flare photometry measurements (a common measure of intraocular inflammation) were taken in a subset of 310 patients (124 in the bimatoprost q.d. group, 123 in the bimatoprost b.i.d. group, and 63 in the timolol group). There were no significant differences among the treatment groups in mean laser-flare photometry readings or in mean changes from baseline. In addition, no increase in flare readings was observed in those patients who developed conjunctival hyperemia during the trial. The results indicate that bimatoprost-induced conjunctival hyperemia is not associated with intraocular inflammation in patients treated for one year. Bimatoprost was also shown to be safe and well-tolerated in the study extension to 2 years (Cohen J S et al., Surv Ophthalmol 2004; 49:S45-S52).

Figure 2:
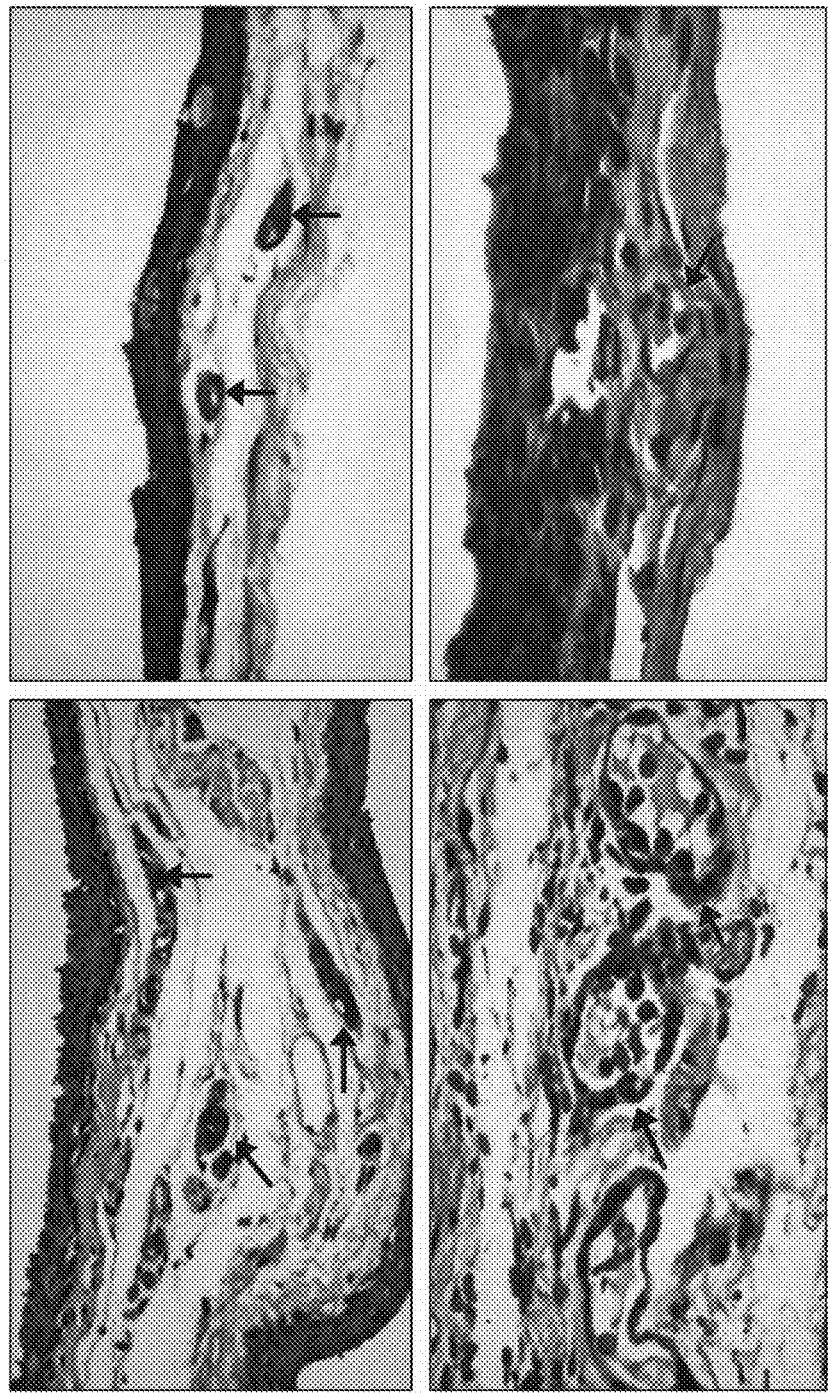
FIG. 2. (Top) Photomicrographs of conjunctival specimens stained with hematoxylin and eosin (H&E, ×200), showing vascular congestion (arrows). (Top left) Specimen from patient 3 of the control group. (Top right) Specimen from patient 4 of the bimatoprost group. (Bottom) Photomicrographs of conjunctival specimens stained with H&E (×400) showing features of acute inflammatory response. (Bottom left) Specimen from patient 1 of the control group, showing vascular congestion with polymorphonuclear leukocyte margination (long arrow), diapedesis phenomenon (short arrow), and inflammatory cell infiltrate. (Bottom right) Specimen from patient 8 of the bimatoprost group, showing vascular congestion with polymorphonuclear leukocyte margination (arrow). Reprinted from FIG. 1 of Leal B C et al, *Am J Ophthalmol* 2004; 138:310-313, with permission from Elsevier.

In a prospective interventional study, histological signs of inflammation were evaluated in conjunctival biopsies from patients with bimatoprost-associated conjunctival hyperemia who were scheduled to undergo cataract surgery (Leal B C et al., Am J Ophthalmol 2004; 138:310-313; FIG. 2). Patients with primary open-angle glaucoma were treated with bimatoprost 0.03% q.d. for 2 to 4 weeks. Nine of 13 eyes treated with bimatoprost developed conjunctival hyperemia and only those eyes were included in the study. The control eyes (n=6) were untreated and had no history of ocular disease other than cataracts. Results showed that signs of inflammation were no more frequent in conjunctival specimens from untreated control patients than in those from bimatoprost-treated patients with trace to moderate hyperemia. Vascular congestion was observed in 83% (⅚) of eyes in the control group and 78% (⅞) of eyes in the bimatoprost treatment group. Signs of inflammatory cell margination or infiltration were present in 33% (2/6) of control eyes compared with 22% (2/9) of bimatoprost-treated eyes and were not related to treatment. The findings of this study demonstrated that bimatoprost-related hyperemia was not associated with histological evidence of inflammation. In another study, bulbar conjunctival biopsies taken at day 7 and impression cytology specimens from patients treated with bimatoprost 0.03% q.d. for 60 days also showed no evidence of inflammation (Mroz M, Abelson M B et al., Invest Ophthalmol Vis Sci 2003; 44:ARVOE-Abstract 4417).

An in vitro study of the expression of various inflammation-associated markers in human cultured conjunctiva-derived epithelial cells was conducted for bimatoprost, along with the prostaglandin FP agonists: latanoprost and travoprost (Guenoun J-M et al., Invest Ophthalmol Vis Sci 2005; 46:2444-2450). None of the drugs appeared to induce direct stimulation of inflammatory pathways involving adhesion molecules or class II antigens. The toxicity observed was mild and primarily related to the concentration of the preservative benzalkonium chloride (BAK). These results are consistent with those obtained from the in-life studies and suggest that conjunctival hyperemia is most likely not an inflammatory response to bimatoprost. Furthermore, it appears too early after onset of treatment to be the inflammatory consequence of long-term treatment.

Pharmacology in Animal Models

Nitric oxide is a predominant second messenger, with a possible compensatory role for potassium channels, in prostaglandin F2a (PGF2a)-induced relaxation of rabbit endothelium-intact jugular veins (Chen J. et al., Br J Pharmacol 1995; 116:3035-3041). The vasorelaxation produced by PGF2a and latanoprost free acid in rabbit submental veins was also found to be mediated by NO and, in addition, by sensory nerves (Astin M, Stjernschantz J., Eur J Pharmacol 1997; 340:195-201). In rabbits, NO and sensory nerves were reported to have roles in PGF2a-induced ocular hyperemia as determined by NOS inhibition and sensory denervation (Astin M, Stjernschantz J, Selén G., Exp Eye Res 1994; 59:401-408; Astin M, Stjernschantz J., Curr Eye Res 1997; 16:886-890). The effects of PGF2a and its analogs, which did not include latanoprost, on ocular surface hyperemia (OSH) in dog eyes correlated with the vasorelaxation in endothelium-intact rabbit precontracted jugular veins (Chen J, Woodward D F. Adv Exp Med Biol 2002; 507:331-336). Taken together, these studies suggest that the pharmacological mechanism of conjunctival hyperemia elicited by bimatoprost and latanoprost may be elucidated by comparing their responses in the isolated jugular vein and conscious dog eyes and using NOS inhibition to determine NO involvement in vasorelaxation and OSH. A methodological difference between these in vitro tissue studies and the in vivo and human in-life studies is that a cyclooxygenase inhibitor such as indomethacin is generally used in the isolated tissue bioassay experiments. Thus, the possibility that products of arachidonic acid cyclooxygenation could be generated de novo and contribute to the vasorelaxation was examined in the rabbit jugular vein preparation.

Effects of Bimatoprost and Latanoprost Free Acid on Rabbit Isolated Jugular Veins The pharmacological mechanism of ocular surface hyperemia elicited by bimatoprost and latanoprost was investigated using the rabbit jugular vein preparation as a quantitative in vitro model (Chen J. et al., Br J Pharmacol 1995; 116:3035-3041). In these studies, tissues were suspended in jacketed organ baths containing Krebs buffer with 1 µM indomethacin (endothelium-intact and -denuded) or in its absence (endothelium-intact) and precontracted with 3 µM histamine. Vasorelaxant and contractile activity were determined as a percentage (%) of the control tone elicited by histamine. Statistical comparisons for the vasorelaxant activity consisted of testing for significance of difference at each of the concentrations tested using the Student'-s t-test for unpaired samples (indomethacin vs no indomethacin) and paired samples (L-NAME vs D-NAME). Differences were considered statistically significant for P-values ≤0.05.

Bimatoprost and latanoprost free acid produced endothelium-dependent vasorelaxant effects that are consistent with and extend previously reported data (Chen J et al., *Invest Ophthalmol Vis Sci* 2004; 45:ARVO E-Abstract 2609; Lumigan (Bimatoprost) Ophthalmic Solution Pharmacology Review of New Drug Application 21-275. FDA/Center for Drug Evaluation and Research. 2001; Part 1 and Part 2:1-107. Available online at http://www.fda.gov/cder/foi/nda/2001/21275_Lumigan.htm). Bimatoprost produced a weak vasorelaxant response ($EC_{50}$=3,981 nM) at high concentrations in endothelium-intact jugular veins and was inactive in the endothelium-denuded preparation (Chen J et al., *Br J Pharmacol* 2005; 144:493-501; FIG. 3A). This response profile is consistent with a wide separation between its IOP lowering and ocular surface hyperemia effects. Bimatoprost produced vasorelaxant responses at the $10^{-6}$ M to $10^{-4}$M concentrations (FIGS. 3A, 5A), which encompassed concentrations ($10^{-6}$-$10^{-5}$ molar equivalent) found in non-human primate ocular surface tissues after single or multiple topical bimatoprost dosing (Woodward D F, Krauss A H-P, Chen J, et al., *J Pharmacol Exp Ther* 2003; 305:772-785; Woodward D F, Phelps R L, Krauss A H-P, et al., *Cardiovasc Drug Rev* 2004; 22:103-120). The weak vasorelaxant response to bimatoprost in the rabbit jugular vein was predictive for the findings of mean mild conjunctival hyperemia in human subjects, although the hyperemia severity may vary according to the tissue concentrations achieved.

Latanoprost free acid produced complex concentration-response curves of maximal vasorelaxation at $10^{-7}$M and a reversal of the relaxant effects at higher concentrations of $10^{-6}$M and $10^{-5}$M in the endothelium-intact preparation and only contractions at the $10^{-5}$M concentration in endothelium-denuded veins (Chen J et al., *Invest Ophthalmol Vis Sci* 2004; 45:ARVO E-Abstract 2609; Lumigan (Bimatoprost) Ophthalmic Solution. Pharmacology Review of New Drug Application 21-275. FDA/Center for Drug Evaluation and Research. 2001; Part 1 and Part 2:1-107. Available online at http://www.fda.gov/cder/foi/nda/2001/21275_Lumigan.htm; FIG. 3B). The response to latanoprost free acid in the jugular veins was interesting in that it produced vasorelaxation at the lower concentrations tested and this response reversed at higher concentrations. This effect, particularly the reversal at high concentrations, may contribute to a decreased ability of latanoprost to elicit ocular surface hyperemia compared to bimatoprost and correlates with its mild conjunctival hyperemia response in humans (Eisenberg D L, Toris C B, Camras C B, *Surv Ophthalmol* 2002; 47:S105-S115; Noecker R S et al., *Am J Ophthalmol* 2003; 135:55-63; Parrish R K, Palmberg P, Sheu W-P., *Am J Ophthalmol* 2003; 135:688-703; Stewart W C et al., *Am J Ophthalmol* 2003; 135:314-320). The vasoconstrictor effects of latanoprost free acid in both the endothelium-intact and -denuded veins suggested the possible involvement of contractile prostanoid TP receptors. However, TP stimulation does not explain reversal of the vasorelaxant response to latanoprost free acid at pharmacological concentrations up to $10^{-6}$ M, since the TP antagonist SQ 29548 used in these studies is highly effective yet did not block the reversal of the vasorelaxant response. Moreover, latanoprost free acid did not contract the endothelium-denuded preparation over the concentration range of $10^{-10}$ to $10^{-6}$ M. Therefore, reversal of the vasorelaxant response to latanoprost free acid in the rabbit jugular vein may involve an endothelial FP receptor or even perhaps a previously unrecognized receptor that causes endothelium-induced vasoconstriction. The increased variability in latanoprost free acid responses at the higher concentrations was likely due to the opposing vasorelaxant and vasoconstrictor effects.

These different activity profiles for latanoprost free acid and bimatoprost in the rabbit jugular vein provide further pharmacological evidence that these agents are recognized by different receptor populations. Latanoprost free acid is a well-known potent and selective prostanoid FP receptor agonist, while bimatoprost is a putative prostamide receptor agonist. Studies using isolated tissue preparations and DNA synthesis in mouse cultured fibroblasts have shown that species-, tissue-, or preparation-related factors, partial agonism, and metabolism all do not provide acceptable explanations of the different activity profiles of bimatoprost and prostanoid FP receptor agonists (Chen J et. al., *Br J Pharmacol* 2005; 144:493-501). The results from the rabbit jugular vein model add support to the contention that bimatoprost is a prostamide and produces its effects by stimulating bimatoprost-sensitive receptors as opposed to prostanoid FP receptors.

Figure 4B:
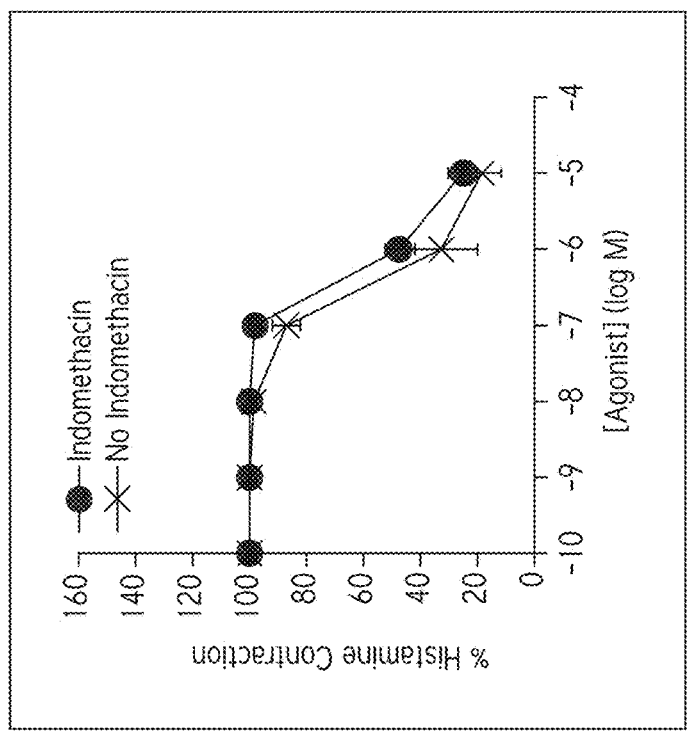
FIG. 4. Concentration-response curves for (FIG. 4A) bimatoprost and (FIG. 4B) latanoprost free acid in the presence or absence of indomethacin in endothelium-intact rabbit isolated jugular veins. Results are expressed as mean±S.E.M. of 7 animals and extend previous results reported in Pharmacology Review of New Drug Application 21-275. FDA/Center for Drug Evaluation and Research. 2001;Part 1 and Part 2:1-107. Available online at http://www.fda.gov/cder/foi/nda/2001/21275_Lumigan.htm.
Figure 4A:
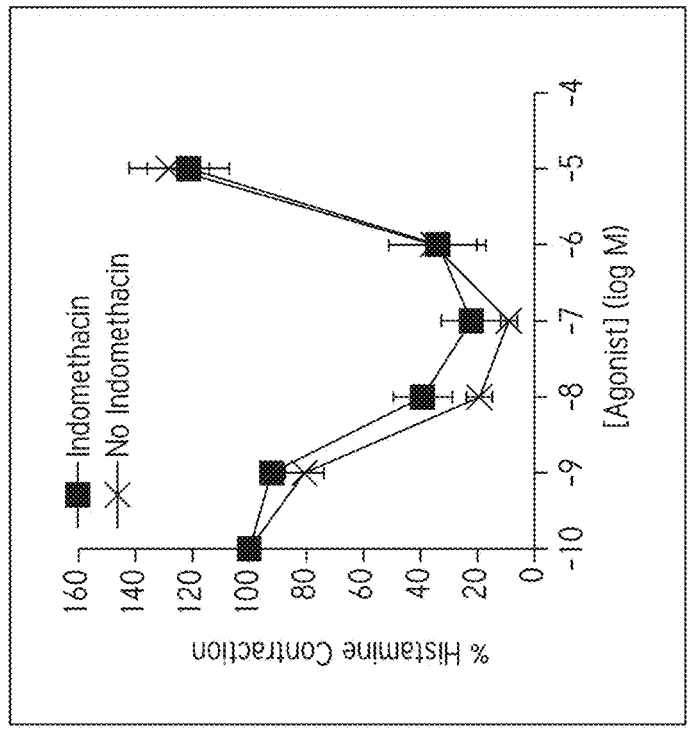

Indomethacin is a cyclooxygenase inhibitor that is routinely used in prostanoid receptor assays (Chen J et al., *Current protocols in pharmacology*. New York: John Wiley & Sons, Inc., 2001; 4.18.1-4.18.41). Studies of intact and viable isolated tissues, such as the rabbit jejunum (Ferreira S H, Herman A G, Vane J R., *Br J Pharmacol* 1976; 56:469-477) and human bronchial muscle (Haye-Legrand I, Cerrina J, Raffestin B et al., *J Pharmacol Exp Ther* 1986; 239:536-541), found the basal output of prostaglandins to be 8-23 pg/mg of tissue at baseline or over 30 min collection periods. In the presence of 1.7 and 2.79 μM indomethacin, the amounts of prostaglandins generated in isolated tissues become negligible (Botting J H, Salzmann R., *Br J Pharmacol* 1974; 50:119-124; Haye-Legrand I, Cerrina J, Raffestin B et al., *J Pharmacol Exp Ther* 1986; 239:536-541). The 1 μM concentration of indomethacin in the tissue bath, in our experience, is sufficient to prevent biosynthesis of prostanoids within isolated vascular tissue preparations (Alster P, Wennmalm Å., *Eur J Pharmacol* 1983; 86:441-446; Chen J et al., *Current protocols in pharmacology*. New York: John Wiley & Sons, Inc., 2001; 4.18.1-4.18.41). At substantially higher concentrations, indomethacin has been reported to lose selectivity for prostanoid biosynthesis inhibition (Aboulafia J et al., *Br J Pharmacol* 1976; 58:223-228; Goodfriend T L, Simpson R U., *Br J Pharmacol* 1981; 72:247-255; Northover B J, *Br J Pharmacol* 1971; 41:540-551; Sawdy R et al., *Br J Pharmacol* 1998; 125:1212-1217). The rabbit jugular vein studies were conducted under experimental conditions of intact isolated tissues continually bathed in buffer containing 1 μM indomethacin. Results of these studies are consistent with and extend previously reported findings (Lumigan (Bimatoprost) Ophthalmic Solution Pharmacology Review of New Drug Application 21-275. FDA/Center for Drug Evaluation and Research. 2001; Part 1 and Part 2:1-107. Available online at http://www.fda.gov/cder/foi/nda/2001/21275_Lumigan.htm). The contractile response to histamine in all of the tissues examined without indomethacin was superimposed with spontaneous spike activity, indicating a contribution of prostaglandin production to the contractions. In the presence of indomethacin, the histamine-induced contractions were well-maintained, stable, and showed minimal spontaneous activity. Endothelium-intact tissues incubated with and without 1 μM indomethacin showed no statistically significant differences in effects between the means and at each of the concentrations tested for bimatoprost and latanoprost free acid (Lumigan (Bimatoprost) Ophthalmic Solution. Pharmacology Review of New Drug Application 21-275. FDA/Center for Drug Evaluation and Research. 2001; Part 1 and Part 2:1-107. Available online at http://www.fda.gov/cder/foi/nda/2001/21275_Lumigan.htm; FIG. 4). These findings suggest that responses to these agents in the rabbit isolated jugular vein are mediated by endothelial located receptors and not by de novo biosynthesis of prostaglandins. Consequently, these in vitro responses can be compared with those observed in the in vivo and in-life studies.

The involvement of nitric oxide in bimatoprost- and latanoprost free acid-induced relaxation of the rabbit jugular vein was determined using L-NAME (L-N$^G$-nitroarginine methyl ester), a potent enantiomerically specific competitive inhibitor of NOS in cell types that include vascular endothelial cells (Koss M C., *Eur J Pharmacol* 1999; 374:161-174; Rees D D et al., *Br J Pharmacol* 1990; 101:746-752), and its inactive isomer D-NAME. In the endothelium-intact histamine precontracted tissues, 100 µM L-NAME significantly inhibited the vasorelaxant responses to bimatoprost and latanoprost free acid, compared to their respective responses in the 100 µM D-NAME control tissues, P≤0.05, paired t-test (FIG. 5). This result indicates that NO is an important contributor to vasorelaxation produced by bimatoprost and latanoprost free acid in the rabbit jugular vein and is consistent with previous findings for PGF$_{2\alpha}$ (Chen J. et al., *Br J Pharmacol* 1995; 116:3035-3041). L-NAME at 100 µM was less effective in inhibiting the responses to PGF$_{2\alpha}$ (Chen J. et al., *Br J Pharmacol* 1995; 116:3035-3041) compared to bimatoprost and latanoprost free acid, which may reflect the selectivity of these agents for their respective receptors.

Effects of Nitric Oxide Synthase Inhibition on Conjunctival Hyperemia in Dog Eye The ocular surface hyperemic effects of bimatoprost, latanoprost (isopropyl ester), or prostaglandin E$_2$ (PGE$_2$) were determined in eyes of conscious dogs treated with topical L-NAME or D-NAME. The dog is suitable for OSH studies since it responds with mild conjunctival hyperemia to bimatoprost and latanoprost, which is consistent with the hyperemic responses observed in humans. The rabbit eye is less predictive for conjunctival hyperemia since latanoprost has no significant acute effects on blood flow in the conjunctiva at a topical dose of 10 µg (0.03%, based on a 30 µl volume) (Astin M, Stjernschantz J, Selén G., *Exp Eye Res* 1994; 59:401-408; Stjernschantz J et al., *Prog Retin Eye Res* 2000; 19:459-496). In vivo experiments consisted of visually grading ocular surface hyperemia (OSH) in conscious Beagle dogs (males or females). All test articles were administered in a masked fashion. The test compound was applied bilaterally as a single drop at time (t)=0 in the one day study. L-NAME 1% (w/v) was topically applied to one eye, while its inactive isomer D-NAME 1% (w/v) was given to the contralateral eye, at 90, 60, 30, 5 min pre-dose, and 1, 2, 3, and 4 h post-dose for a total of 8 drops (approximately 2.8 mg) each per animal. OSH grading was semi-quantitative and assessed according to a 5-point scoring scale used for clinical evaluations: 0=none; 0.5=trace; 1=mild; 2=moderate; and 3=severe. The statistical comparisons for OSH in the dog eyes consisted of testing for significance of mean differences from baseline at each time point using the Wilcoxon signed-rank test for paired observations. Differences were considered statistically significant for P-values ≤0.05.

Figure 6A:
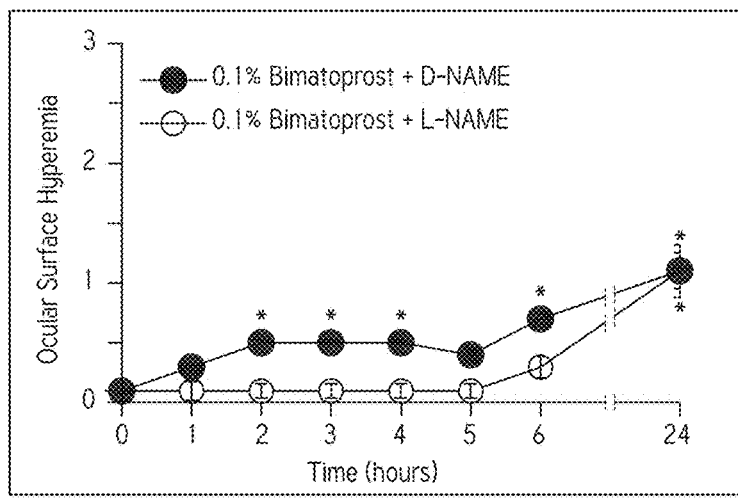
FIG. 6. Effects of L-NAME (test eye) and D-NAME control (contralateral fellow eye) on ocular surface hyperemia elicited by (FIG. 6A) 0.1% bimatoprost, (FIG. 6B) 0.005% latanoprost, or (FIG. 6C) 0.01% $PGE_2$, topically applied to both eyes of each dog at time 0. Values are expressed as mean±S.E.M. of 8 animals. *$P \leq 0.05$, difference from baseline (time 0), Wilcoxon signed-rank test for paired observations. Data from Chen J et al., *Invest Ophthalmol Vis Sci* 2004; 45:ARVO E-Abstract 2609.
Figure 6B:
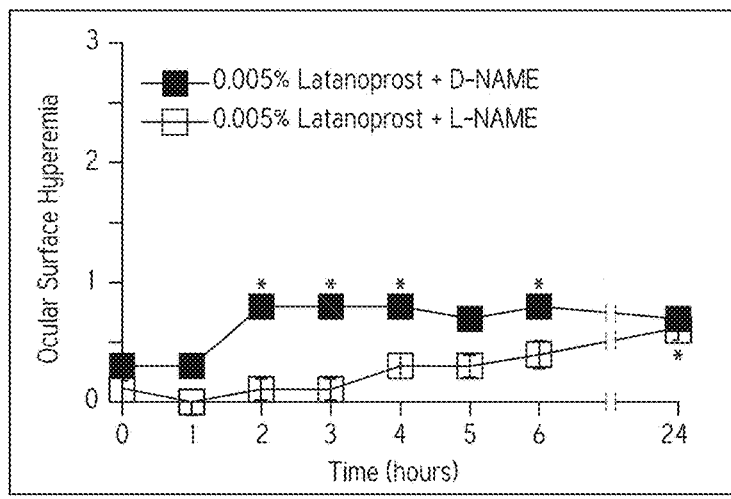

L-NAME and D-NAME did not produce conjunctival hyperemia or any adverse ocular effects at baseline (time 0). Our studies using direct evaluation of L-NAME on conjunctival hyperemia in dogs indicated the involvement of NO in OSH elicited by bimatoprost and latanoprost (Chen J et al., *Invest Ophthalmol Vis Sci* 2004; 45:ARVO E-Abstract 2609; FIG. 6A, 6B). The hyperemia effects elicited by bimatoprost 0.1% and latanoprost 0.005% were blocked in eyes treated with L-NAME, as shown by responses that were not different from the respective paired baseline values at 0-6 h of the study. In D-NAME treated control dog eyes, bimatoprost and latanoprost elicited trace to mild ocular surface hyperemic responses that were significantly different compared to baseline (P≤0.05). The inhibition by L-NAME in dog eyes and the in vitro rabbit jugular vein model for OSH suggests that NO is the predominant mediator of OSH for bimatoprost. L-NAME treatment also inhibited latanoprost-induced conjunctival hyperemia in dog eyes but, in this case, the D-NAME treated eyes were unaffected. This finding may possibly reflect a partial role for NO in latanoprost-induced OSH, since the vasorelaxant effects in rabbit submental veins were shown to be mediated by NO, calcitonin gene-related peptide, substance P or another tachykinin released from perivascular sensory nerves (Astin M, Stjernschantz J., *Eur J Pharmacol* 1997; 340:195-201; Stewart W C et al., *Am J Ophthalmol* 2003; 135:314-320).

Figure 6C:
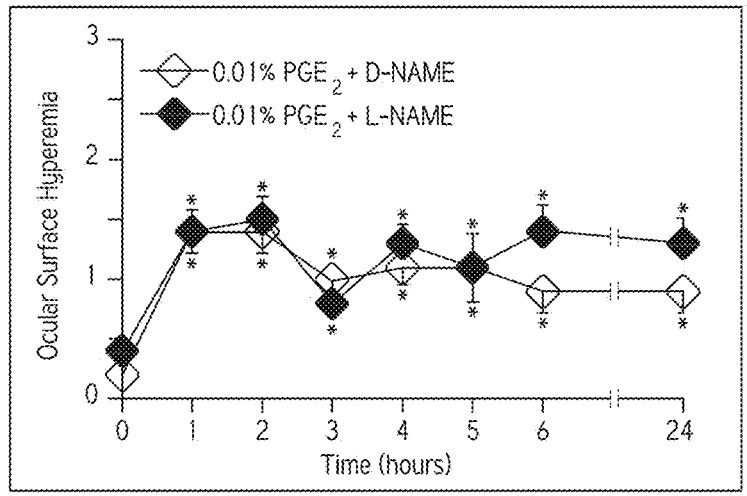

In these studies, PGE$_2$ 0.01% served as a comparator. It produced OSH of mild to moderate severity; its effects were significantly different from those at the baseline (P≤0.05) in both the D-NAME- and L-NAME-treated eyes (Chen J et al., *Invest Ophthalmol Vis Sci* 2004; 45:ARVO E-Abstract 2609; FIG. 6C). The finding that L-NAME had no effect on the observed conjunctival hyperemia was predicted, since PGE$_2$ does not require an intact vascular endothelium to exert its relaxant response (Chen J. et al., *Br J Pharmacol* 1995; 116:3035-3041). These results showed that the nitric oxide synthase inhibitor L-NAME inhibits the in vivo acute OSH response to bimatoprost or latanoprost, but has no effect on PGE$_2$-induced OSH.

In-Life Observation and Histopathological Assessment

The ocular surface safety following bimatoprost treatment was addressed using rabbits, dogs, and non-human primates in studies of one month to one year duration. Results of the studies were submitted to worldwide regulatory authorities for the approval of bimatoprost as an antiglaucoma drug (Lumigan (Bimatoprost) Ophthalmic Solution. Pharmacology Review of New Drug Application 21-275. FDA/Center for Drug Evaluation and Research. 2001; Part 1 and Part 2:1-107. Available online at http://www.fda.gov/cder/foi/nda/2001/21275_Lumigan.htm). The possible involvement of ocular surface inflammation in animal eyes treated with subclinical, clinical, and exaggerated doses of bimatoprost and controls were evaluated by in-life observations and histopathological assessment. The in-life ocular evaluations consisted of clinical observations, gross ocular observations, ophthalmoscopy, and slit lamp biomicroscopy. Histopathological assessments were conducted by three board-certified veterinary pathologists, each applying somewhat different criteria and terminology, in separate studies. The animals comprised of those scheduled for terminal sacrifice and similar numbers of males and females were used in each group. As part of a comprehensive assessment of the eye, tissues from the upper and lower eyelids with associated palpebral conjunctiva were excised for histopathological evaluation. Ocular tissues were preserved in 10% formalin, processed to paraffin, sectioned at 5 microns, and stained using H&E. The tissues were sectioned in an anatomically consistent manner for all animals in all groups. One section was evaluated for each designated site.

Rabbit Studies

The rabbit is the species most frequently used in eye irritation tests. New Zealand White (albino) rabbits were assigned to 4 groups (n=16 per group) for a one month study (Table 13). The animals received four times daily (q.i.d.) topical applications of vehicle or bimatoprost (0.001%, 0.01%, 0.1%) in the left eye, while the right eye was untreated.

TABLE 13

Incidence of minimal-to-mild mononuclear cell infiltration in palpebral conjunctiva of albino rabbits (n = 16 in each group) after daily application of bimatoprost, q.i.d. for one month

| | Groups | | | | | | | |
|---|---|---|---|---|---|---|---|---|
| | 1 | | 2 | | 3 | | 4 | |
| | Eyes | | | | | | | |
| Treatment | Left Vehicle | Right Untreated Control | Left Bimatoprost 0.001% | Right Untreated control | Left Bimatoprost 0.01% | Right Untreated Control | Left Bimatoprost 0.1% | Right Untreated control |
| Upper Eyelid | 1 | 3 | 4 | 3 | 6 | 4 | 8 | 6 |
| Lower Eyelid | 15 | 12 | 12 | 10 | 13 | 15 | 14 | 14 |

Incidence: number of animals with histopathologic findings
q.i.d. = four times daily; Study 2968-58. Adapted from ref. 31.

Dutch-Belted (pigmented) rabbits were assigned to 2 groups (n=19-20 per group) and received twice daily (b.i.d.) topical ocular applications of vehicle or bimatoprost 0.03% in the left eye for one month (Table 14). The right eye was untreated. The vehicle and drug solutions were preserved with 0.005% benzalkonium chloride (BAK).

TABLE 14

Incidence of mononuclear cell infiltration in palpebral conjunctiva of pigmented rabbits after daily application of bimatoprost, b.i.d. for one month

| | Groups | | | |
|---|---|---|---|---|
| | 1 (n = 20) | | 2 (n = 19) | |
| | Eyes | | | |
| Treatment | Left Vehicle | Right Untreated Control | Left Bimatoprost 0.03% | Right Untreated Control |
| Upper Eyelid | | | | |
| Minimal/mild | 10 | 10 | 6 | 14 |
| Lower Eyelid | | | | |
| Minimal/mild | 16 | 15 | 12 | 13 |
| Moderate | 1 | 0 | 0 | 0 |

Incidence: number of animals with histopathologic findings;
n = number of animals per group.
b.i.d. = twice daily; Study TX97032. Adapted from ref. 31.

In a six month study, Dutch-Belted (pigmented) rabbits were assigned to 4 groups (n=20 per group) (Table 15). The left eye received b.i.d. topical ocular applications of vehicle, once daily (q.d.) or b.i.d. bimatoprost 0.03%, or b.i.d. bimatoprost 0.1%. The right eye was untreated. The vehicle and drug solutions were preserved with 0.005% BAK.

TABLE 15

Mononuclear cell infiltration in palpebral conjunctiva of pigmented rabbits (n = 20 per group) after daily application of bimatoprost, q.d. or b.i.d. for 6 months

| | Groups | | | | | | | |
|---|---|---|---|---|---|---|---|---|
| | 1 | | 2 | | 3 | | 4 | |
| | Eyes | | | | | | | |
| Treatment | Left Vehicle b.i.d. | Right Untreated Control | Left Bimatoprost 0.03% q.d. | Right Untreated control | Left Bimatoprost 0.03.% b.i.d. | Right Untreated Control | Left Bimatoprost 0.1% b.i.d. | Right Untreated Control |
| Upper Eyelid | N | N | N | N | N | N | N | N |
| Lower Eyelid | N | N | N | N | N | N | N | N |

N = Tissues within normal histological limits
q.d. = once daily;b.i.d. - twice daily; Study TX98004. Adapted from ref. 31.

Dog Study

Beagle dogs are recognized as appropriate for use in multiple-dose ocular irritation and safety studies. In a one month study, Beagle dogs were assigned to 4 groups (n=6 per group) (Table 16). The left eye was treated with q.i.d. topical ocular applications of vehicle or bimatoprost at 0.001%, 0.01%, or 0.1% doses and the right eye was untreated. All test solutions were non-preserved.

Summary of in-Life Observations and Histopathological Assessments

No compound-related findings of corneal toxicity, discomfort or irritation, or histopathological changes were observed in eyes of the animal species treated with multiple subclinical, clinical, and exaggerated doses of bimatoprost. Histopathological evaluations of eyes treated with the highest dose and frequency of application of bimatoprost in each study were compared to vehicle treatment. The results are

TABLE 16

Incidence of minimal-to-mild mononuclear cell infiltration in palpebral conjunctiva of dogs (n = 6 per group) after daily application of bimatoprost, q.i.d. for one month.

| | Groups | | | | | | | |
|---|---|---|---|---|---|---|---|---|
| | 1 | | 2 | | 3 | | 4 | |
| | Eyes | | | | | | | |
| Treatment | Left Vehicle | Right Untreated Control | Left Bimatoprost 0.001% | Right Untreated Control | Left Bimatoprost 0.01% | Right Untreated Control | Left Bimatoprost 0.1% | Right Untreated Control |
| Upper Eyelid | 5 | 5 | 4 | 4 | 3 | 5 | 5 | 3 |
| Lower Eyelid | 5 | 5 | 3 | 4 | 5 | 5 | 6 | 6 |

Incidence: number of animals with histopathologic findings
q.i.d. = four times daily; Study 3137-5. Adapted from ref. 31.

Non-Human Primate Study

Cynomolgus monkeys have been historically used in safety evaluation studies and are recommended by most regulatory agencies. In a 12 month study, Cynomolgus monkeys scheduled for terminal sacrifice were assigned to 4 groups (n=6-8 per group) (Table 17). The right eyes were treated with topical ocular applications of vehicle b.i.d., bimatoprost 0.03% q.d., bimatoprost 0.03% b.i.d., or bimatoprost 0.1% b.i.d. The left eye was not treated. All test solutions were preserved with 0.005% BAK.

summarized in Table 18. Only vehicle-treated eyes showed inflammatory changes above background stimulation in the palpebral conjunctiva, whereas no such changes were related to bimatoprost treatment. The presence of minimal to mild inflammatory infiltrates (background stimulation) in conjunctiva of untreated control eyes, vehicle-treated eyes, and bimatoprost-treated eyes was considered to be incidental and unrelated to treatment. In all the studies, bimatoprost did not increase the intensity or alter the characteristics of inflammatory processes in the conjunctiva.

TABLE 17

Incidence of inflammation in palpebral conjunctiva of cynomolgus monkeys after daily application of bimatoprost, q.d. or b.i.d. for 12 months.

| | Groups | | | | | | | |
|---|---|---|---|---|---|---|---|---|
| | 1 (n = 6) | | 2 (n = 8) | | 3 (n = 6) | | 4 (n-6) | |
| | Eyes | | | | | | | |
| Treatment | Left Untreated control | Right Vehicle b.i.d. | Left Untreated control | Right Bimatoprost 0.03% q.d. | Left Untreated control | Right Bimatoprost 0.03% b.i.d. | Left Untreated control | Right Bimatoprost 0.1% b.i.d. |
| Upper Eyelid | | | | | | | | |
| Chronic active Lower Eyelid | 5 | 5 | 4 | 4 | 3 | 5 | 5 | 3 |
| Subacute Chronic active | | | | | | | | |

Incidence: number of animals with histopathologic findings;
n = number of animals per group.
q.d. = once daily; b.i.d. = twice daily; Study 6177-110. Adapted from ref. 31.

TABLE 18

Summary of incidence of histopathologic findings above
background stimulation in the lower palpebral conjunctiva
after topical administration of bimatoprost

| Species | Strain | Duration months | Highest dose & frequency tested | Incidence of inflammatory infiltrates above background |
|---|---|---|---|---|
| Rabbits | New Zealand White | 1 | 0.1% q.i.d. Vehicle | 0 (16) 0 (16) |
| Rabbits | Dutch-Belted | 1 | 0.03% b.i.d. Vehicle | 0 (19) 1 (20) |
| Rabbits | Dutch-Belted | 6 | 0.1% b.i.d. Vehicle | 1 (20) 0 (20) |
| Dogs | Beagle | 1 | 0.1% q.i.d. Vehicle | 0 (6) 0 (6) |
| Monkeys | Cynomolgus | 12 | 0.1% b.i.d. Vehicle | 0 (60) 1 (6) |

Incidence: number of animals with histopathologic findings (per total number of animals)
Adapted from ref. 31.

The in-life evaluations indicated no treatment-related ocular surface inflammation in animals treated with bimatoprost for periods of up to one year exposure. Minimal to mild mononuclear infiltrates were recognizable in routine sampling of the conjunctiva of untreated and treated laboratory animals. Such changes represent background stimulation of this mucosal barrier. Thus, across all studies and species, the results indicated that bimatoprost does not increase the intensity or alter the characteristics of inflammatory processes in the conjunctiva of animals. These findings are more in agreement with a protective role for eNOS rather than involvement in pro-inflammatory processes. The safety evaluation results for animals treated with bimatoprost correlate with the clinical assessments suggesting that bimatoprost-related conjunctival hyperemia occurs by a non-inflammatory mechanism (Abelson M B et al., Adv Ther 2003; 20:1-13; Guenoun J-M et al., Invest Ophthalmol Vis Sci 2005; 46:2444-2450; Higginbotham E J, Schuman J S, Goldberg I, et al., Arch Ophthalmol 2002; 120:1286-1293; Leal B C et al., Am J Ophthalmol 2004; 138:310-313; Lumigan (Bimatoprost) Ophthalmic Solution. Pharmacology Review of New Drug Application 21-275. FDA/Center for Drug Evaluation and Research. 2001; Part 1 and Part 2:1-107. Available online at http://www.fda.gov/cder/foi/nda/2001/21275_Lumigan.htm; Mroz M, Abelson M B et al., Invest Ophthalmol Vis Sci 2003; 44:ARVOE-Abstract 4417; Noecker R S et al., Am J Ophthalmol 2003; 135:55-63).

CONCLUSIONS

The results of pharmacological studies of OSH indicate that bimatoprost and latanoprost elicit conjunctival hyperemia by a common signaling mechanism that involves intracellular calcium and endothelial-derived nitric oxide. Extensive safety evaluation studies of bimatoprost at clinical and exaggerated doses in three species of laboratory animals found no evidence of treatment-related ocular surface inflammation. The results showed that bimatoprost has a very high safety margin and is well-tolerated in animals.
Clinical Studies with Bimatoprost in Combination with Timolol Approximately 60% of patients being treated for glaucoma require two or more agents (adjuvant therapy) to control the intraocular pressure. For this reason, combination therapies, in which two pharmaceutically active agents are combined in the same formulation, have been developed to decrease complexity in the treatment regimen, improve patient compliance, and to minimize the exposure to excipients with possible toxicity such as benzalkonium chloride. Currently, the most commonly prescribed adjuvant therapy includes a beta-blocker and a prostaglandin analogue. For this reason, Allergan has formulated bimatoprost 0.03% together with timolol 0.5% (Combination). To date, four pivotal clinical trials have been conducted that compares the combination with monotherapy (bimatoprost 0.03% once a day given individually) Unexpectedly, there were substantial reductions in the degree of ocular surface hyperemia observed with the combination compared with monotherapy as reported as adverse events or treatment-related adverse events in the pooled data from the 018T and 021T studies as well as from the 026T study (table) suggesting that the timolol may have been responsible for the decrease in hyperemia.

TABLE 19

Phase 3 Studies: Incidence of Conjunctival hyperaemia Detected on
Biomicroscopy and Reported as a Treatment-Related AE for
Patients in the Combination Group

| | Combination | | Bimatoprost | |
|---|---|---|---|---|
| | Biomicro ≥ +1 | Rx-rel AE | Biomicro ≥ +1 | Rx-rel AE |
| Pooled 192024-018T & 021T (3 months) | 15.6%[a] | 22.7%[a] | 30.9% | 38.5% |
| Pooled 192024-018T & 021T (3 months) | 22.1%[a] | 25.7%[a] | 41.5% | 43.4% |
| 192024-504T (3 months) | 20.4% | 25.0% | 21.1% | 29.9% |
| 192024-026T (3 weeks) | 8.5% | 19.3% | 18.9% | 27.8% |

[a]Combination statistically significantly lower than Bimatoprost (p ≤ 0.024)

The mechanism of the effect is not certain; however, it is well-known that beta blockade can induce an unopposed alpha agonism leading to vasoconstriction and decrease ocular hyperemia. (see first two reference at the end) More recently, it has been shown that nitric oxide synthase is under beta-adrenergic control. This suggests that beta-blockade should decrease the production of nitric oxide resulting from the topical exposure of the prostaglandin analogue to the ocular surface reducing the severity of ocular surface hyperemia (the remainder of references at the end of the document).

What is claimed is:

1. A composition comprising a prostaglandin agent and a vasoconstrictor agent, wherein said composition is an ophthalmic pharmaceutical formulation further comprising an ophthalmically acceptable excipient, and wherein said vasoconstrictor agent is present in a sub-therapeutic amount, and wherein said prostaglandin agent and said vasoconstrictor agent are present in a combined amount effective to treat an ophthalmic disease, and wherein said prostaglandin agent is bimatoprost, and wherein said bimatoprost is present in an amount of about 0.01% w/w.

2. The composition of claim 1, wherein said ophthalmic pharmaceutical formulation is a gel formulation.

3. The composition of claim 1, wherein said ophthalmic pharmaceutical formulation is an aqueous solution.

4. The composition of claim 1, wherein said vasoconstrictor agent is an alpha adrenergic agonist.

5. The composition of claim 1, wherein said vasoconstrictor agent is selected from the group consisting of befunolol, betaxolol, carteolol, levobunolol, metipranolol, timolol, brimonidine, tetrahydrozolone hydrochloride and mepindolol.

6. The composition of claim 5, wherein the vasoconstrictor agent is timolol.

7. The composition of claim 5, wherein the vasoconstrictor agent is befunolol.

8. The composition of claim 5, wherein the vasoconstrictor agent is betaxolol.

9. The composition of claim 5, wherein the vasoconstrictor agent is carteolol.

10. The composition of claim 5, wherein the vasoconstrictor agent is levobunolol.

11. The composition of claim 5, wherein the vasoconstrictor agent is metipranolol.

12. The composition of claim 5, wherein the vasoconstrictor agent is brimonidine.

13. The composition of claim 5, wherein the vasoconstrictor agent is tetrahydrozolone hydrochloride.

14. The composition of claim 5, wherein the vasoconstrictor agent is mepindolol.

* * * * *

UNITED STATES PATENT AND TRADEMARK OFFICE
CERTIFICATE OF CORRECTION

PATENT NO. : 9,579,328 B2  Page 1 of 2
APPLICATION NO. : 14/990289
DATED : February 28, 2017
INVENTOR(S) : Rhett M. Schiffman et al.

It is certified that error appears in the above-identified patent and that said Letters Patent is hereby corrected as shown below:

On the Title Page

In item (56), in Column 2, under "Other Publications", Line 25, delete "Rrest" and insert -- Rest --, therefor.

In item (56), in Column 2, under "Other Publications", Line 27, delete "Phamacology/" and insert -- Pharmacology/ --, therefor.

In item (56), in Column 2, under "Other Publications", Line 35, delete "Bristish" and insert -- British --, therefor.

In item (56), in Column 2, under "Other Publications", Line 35, delete "Dermtatology," and insert -- Dermatology, --, therefor.

On the page 2, in Column 1, under "Other Publications", Line 25, delete "Latanprost," and insert -- Latanoprost, --, therefor.

On the page 2, in Column 2, under "Other Publications", Line 36, delete "Progess" and insert -- Progress --, therefor.

In the Specification

In Column 4, Line 20, delete "tetrahydrozolone" and insert -- tetrahydrozoline --, therefor.

In Column 8, Line 19, after "amounts" insert -- . --.

In Column 8, Line 57, delete "naphthylanesulfonic" and insert -- naphthalenesulfonic --, therefor.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*

In Column 9, Lines 15-17, delete "A "third" component is different from the other, first, and second components, and further enumerated or "additional" components are similarly different." and insert the same on Column 9, Line 14 as a continuation of the same paragraph.

In Column 14, Line 33, delete "-3yl)" and insert -- -3-yl) --, therefor.

In Column 19, Line 56, before "for" delete "to".

In Column 20, Line 16, delete "carageenan" and insert -- carrageenan --, therefor.

In Column 37, Line 67, delete ":5353-" and insert -- :S353- --, therefor.

In Column 41, Line 5, delete "Solution" and insert -- Solution. --, therefor.

In Column 41, Line 16, delete "$10^{-4}M$" and insert -- $10^{-4}$ M --, therefor.

In Column 41, Line 28, delete "$10^{-7}M$" and insert -- $10^{-7}$ M --, therefor.

In Column 41, Line 30, delete "$10^{-6}M$" and insert -- $10^{-6}$ M --, therefor.

In Column 41, Line 30, delete "$10^{-5}M$" and insert -- $10^{-5}$ M --, therefor.

In Column 41, Line 31, delete "$10^{-5}M$" and insert -- $10^{-5}$ M --, therefor.

In Column 42, Line 10, delete "et." and insert -- et --, therefor.

In Column 42, Lines 46-47, delete "Solution" and insert -- Solution. --, therefor.

In Column 43, Line 62, delete "FIG." and insert -- FIGS. --, therefor.

In Columns 45-46, Line 14 (in Table 15), delete "daily;b.i.d." and insert -- daily; b.i.d. --, therefor.

In Columns 47-48, Line 4 (in Table 17), delete "4 (n-6)" and insert -- 4 (n = 6) --, therefor.

In the Claims

In Column 50, Line 66, in Claim 5, delete "tetrahydrozolone" and insert -- tetrahydrozoline --, therefor.

In Column 51, Line 16, in Claim 13, delete "tetrahydrozolone" and insert -- tetrahydrozoline --, therefor.